US012697283B2

(12) United States Patent
Townley et al.

(10) Patent No.: US 12,697,283 B2
(45) Date of Patent: Aug. 4, 2026

(54) SMART DRUG SELECTION AND DISPENSING SYSTEM AND METHOD

(71) Applicant: Rightis, Inc., Minneapolis, MN (US)

(72) Inventors: Patrick Townley, Minneapolis, MN (US); Brian Lucas, Norwich, VT (US)

(73) Assignee: Rightis, Inc., Minneapolis, MN (US)

( * ) Notice: Subject to any disclaimer, the term of this patent is extended or adjusted under 35 U.S.C. 154(b) by 356 days.

(21) Appl. No.: 18/394,384

(22) Filed: Dec. 22, 2023

(65) Prior Publication Data

US 2024/0207140 A1 Jun. 27, 2024

Related U.S. Application Data

(60) Provisional application No. 63/476,827, filed on Dec. 22, 2022.

(51) Int. Cl.
| | |
|---|---|
| *A61J 3/07* | (2006.01) |
| *G16H 10/60* | (2018.01) |
| *G16H 20/13* | (2018.01) |

(52) U.S. Cl.
CPC ................ *A61J 3/07* (2013.01); *G16H 10/60* (2018.01); *G16H 20/13* (2018.01)

(58) Field of Classification Search
CPC ............ A61J 3/07; G16H 10/60; G16H 20/13
See application file for complete search history.

(56) References Cited

U.S. PATENT DOCUMENTS

| | | | | |
|---|---|---|---|---|
| 5,558,638 A | * | 9/1996 | Evers ................... | A61B 5/4362 |
| | | | | 604/66 |
| 5,710,551 A | | 1/1998 | Ridgeway | |

(Continued)

FOREIGN PATENT DOCUMENTS

| | | |
|---|---|---|
| WO | 0017799 A1 | 3/2000 |
| WO | 0032097 A1 | 6/2000 |

(Continued)

OTHER PUBLICATIONS

International Search Report and Written Opinion of the International Searching Authority, the European Patent Office, issued in related international application No. PCT/US2023/085697 on May 6, 2024, 15 pages.

(Continued)

*Primary Examiner* — Michael Collins
(74) *Attorney, Agent, or Firm* — Gesmer Updegrove LLP; Arthur J. O'Dea

(57) ABSTRACT

An integrated drug selection system centered around point-of-care dispensing assembly that provides a practical, cost effective, and convenient way to optimize and individualize drug treatments. Through the cloud-based platform the dispensing assembly can be linked to the patient-user, prescriber-user, pharmacy-user, and the like, via network communication protocols and techniques. The dispensing assembly can include a drug reservoir assembly and a drug dispensing section (or base). The drug reservoir assembly is rotated between one or more rotatable drug reservoirs to dispense different drugs. The system includes a cloud-based platform that uses software to process and facilitate dispensing, treatments, data, monitoring, notifications, and trials, including treatment of specific health conditions.

20 Claims, 16 Drawing Sheets

(56) References Cited

U.S. PATENT DOCUMENTS

| | | | |
|---|---|---|---|
| 6,394,306 B1 | 5/2002 | Pawlo et al. |
| 6,411,567 B1 | 6/2002 | Niemiec et al. |
| 6,574,166 B2 | 6/2003 | Niemiec |
| 7,048,141 B2 | 5/2006 | Abdulhay et al. |
| 7,909,207 B2 | 3/2011 | Handfield et al. |
| 8,014,232 B2 | 9/2011 | Niemiec et al. |
| 8,193,918 B1 | 6/2012 | Shavelsky et al. |
| 8,417,378 B2 | 4/2013 | Joslyn |
| 8,744,620 B2 | 6/2014 | Shavelsky et al. |
| 8,977,390 B2 | 3/2015 | Jefferies et al. |
| 9,211,233 B2 | 12/2015 | Shavelsky et al. |
| 9,358,499 B2 | 6/2016 | Akdogan et al. |
| 9,358,500 B2 | 6/2016 | Akdogan et al. |
| 9,463,412 B2 | 10/2016 | Akdogan et al. |
| 9,489,493 B2 | 11/2016 | Jefferies et al. |
| 9,501,887 B2 | 11/2016 | Berg et al. |
| 9,533,300 B2 | 1/2017 | Richter |
| 9,550,619 B2 | 1/2017 | Park, IV |
| 9,731,853 B2 | 8/2017 | Akdogan et al. |
| 9,836,583 B2 | 12/2017 | García et al. |
| 10,102,706 B2 | 10/2018 | Jefferies et al. |
| 10,106,283 B2 | 10/2018 | Akdogan et al. |
| 10,173,380 B2 | 1/2019 | Groetzschel |
| 10,360,751 B2 | 7/2019 | Berg et al. |
| 10,555,874 B2 | 2/2020 | Feng et al. |
| 10,685,091 B1 | 6/2020 | Park, IV et al. |
| 10,723,541 B2 | 7/2020 | Akdogan et al. |
| 10,730,687 B2 | 8/2020 | MacVittie et al. |
| 10,751,239 B2 | 8/2020 | Volek et al. |
| 11,160,730 B2 | 11/2021 | Townley |
| 2005/0076969 A1 | 4/2005 | Tahil et al. |
| 2010/0096399 A1 | 4/2010 | Ratnakar |
| 2016/0039553 A1* | 2/2016 | Akdogan ............... G16H 20/13 |
| | | | 700/240 |
| 2016/0107820 A1 | 4/2016 | MacVittie et al. |
| 2018/0228695 A1 | 8/2018 | Valentine |
| 2020/0350073 A1 | 11/2020 | Goldsmith et al. |
| 2023/0248614 A1* | 8/2023 | Aon ...................... A61J 7/0418 |
| | | | 700/242 |

FOREIGN PATENT DOCUMENTS

| | | | |
|---|---|---|---|
| WO | 0072452 A2 | 11/2000 |
| WO | 2013025520 A2 | 2/2013 |
| WO | 2019241282 A1 | 12/2019 |
| WO | 2020092338 A1 | 5/2020 |

OTHER PUBLICATIONS

International Preliminary Report on Patentability issued by the International Bureau of WIPO in corresponding international application No. PCT/US2023/085697 on Jun. 24, 2025, 11 pages.

* cited by examiner

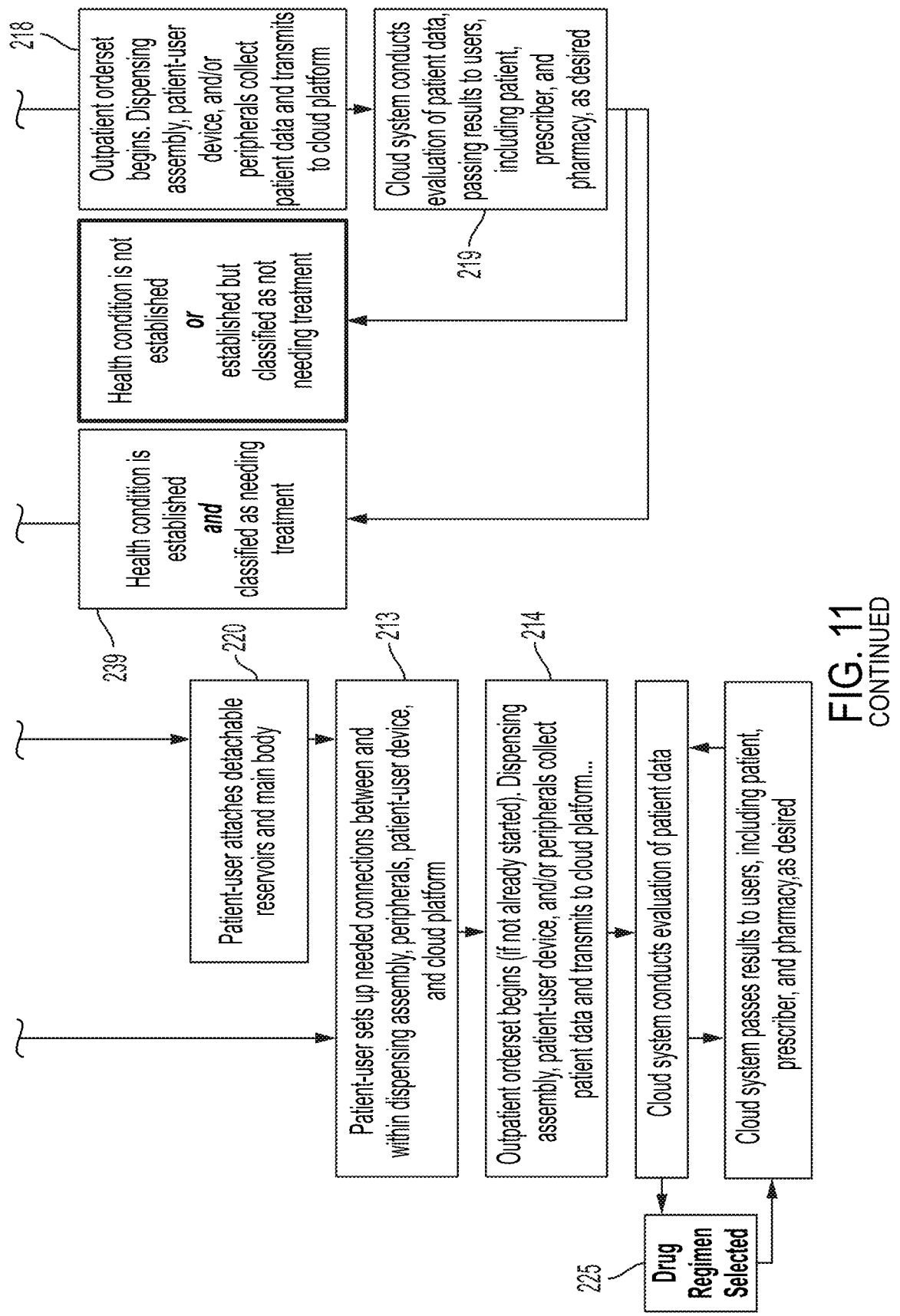

218   Outpatient orderset begins. Dispensing assembly, patient-user device, and/or peripherals collect patient data and transmits to cloud platform 219   Cloud system conducts evaluation of patient data, passing results to users, including patient, prescriber, and pharmacy, as desired Health condition is not established *or* established but classified as not needing treatment 239   Health condition is established *and* classified as needing treatment 220   Patient-user attaches detachable reservoirs and main body 213   Patient-user sets up needed connections between and within dispensing assembly, peripherals, patient-user device, and cloud platform 214   Outpatient orderset begins (if not already started). Dispensing assembly, patient-user device, and/or peripherals collect patient data and transmits to cloud platform...

Cloud system conducts evaluation of patient data

Cloud system passes results to users, including patient, prescriber, and pharmacy, as desired 225   Drug Regimen Selected

FIG. 11
CONTINUED

Statistics of Inputs and Outcomes by Bayesian Classification—Illustrative embodiment of High Blood Pressure[a]

| $n$—Period[b] | Prior (0) | | | Data (D) | | | Posterior (1) | | |
|---|---|---|---|---|---|---|---|---|---|
| | Mean | Variance[c] | Info-Weight[e] | Trust-weighted sample average | Trust-weighted sample variance[c,d] | Trust-weight[e] | Mean | Variance[c] | Info-Weight[e] |
| | $\mu_{p0}$ | $\sigma^2_{p0}$ | $i_{p0}$ | $\bar{x}_{pD}$ | $S^2_{pD}$ | $t_{pD}$ | $\mu_{p1}$ | $\sigma^2_{p1}$ | $i_{p1}$ |

0—Placebo Run-In

Home or office values — patient's average — patient's variance[f] — 19

Stage-specific midpoint Unknown — 134.5 (stage 1) population[h]; 150 (stage 2) population[h]; population[h] — 1; 1

$$\bar{x}_{pDx} = $$

$$S^2_{pDx} = $$

$$\mu_{p1x} = $$

$$\sigma^2_{p1x} = $$

$$\mu_{p1x} = \frac{\sum(S/T_{pDx} \cdot t_{pDx}) \sum(S/T_{pDx} \cdot \bar{x}_{pDx})^2 \sum t_{pDx} (\mu_{p0} \cdot i_{p0}) + (\bar{x}_{pDx} \cdot \sum t_{pDx}) (\sigma^2_{p0} \cdot i_{p0}) + [S^2_{pDx} (\sum t_{pDx} - 1)] +}{\sum t_{pDx}} \cdot \frac{(\sum t_{pDx})}{(\sum t_{pDx}) - 1} \cdot \frac{i_{p0} + \sum t_{pDx}}{i_{p1x}}$$

$$\sigma^2_{p1x} = \frac{\left[ i_{p0} \sum t_{pDx} (\bar{x}_{pDx} - \mu_{p0})^2 \right]}{i_{p1x}} \cdot \frac{1}{i_{p0} + \sum t_{pDx}}$$

p—p[th] Treatment

Priors from placebo run-in period — $\mu_{p0} = \mu_{01}$   $\sigma^2_{p0} = \sigma^2_{01}$   $i_{p0} = i_{01}$

FIG. 12

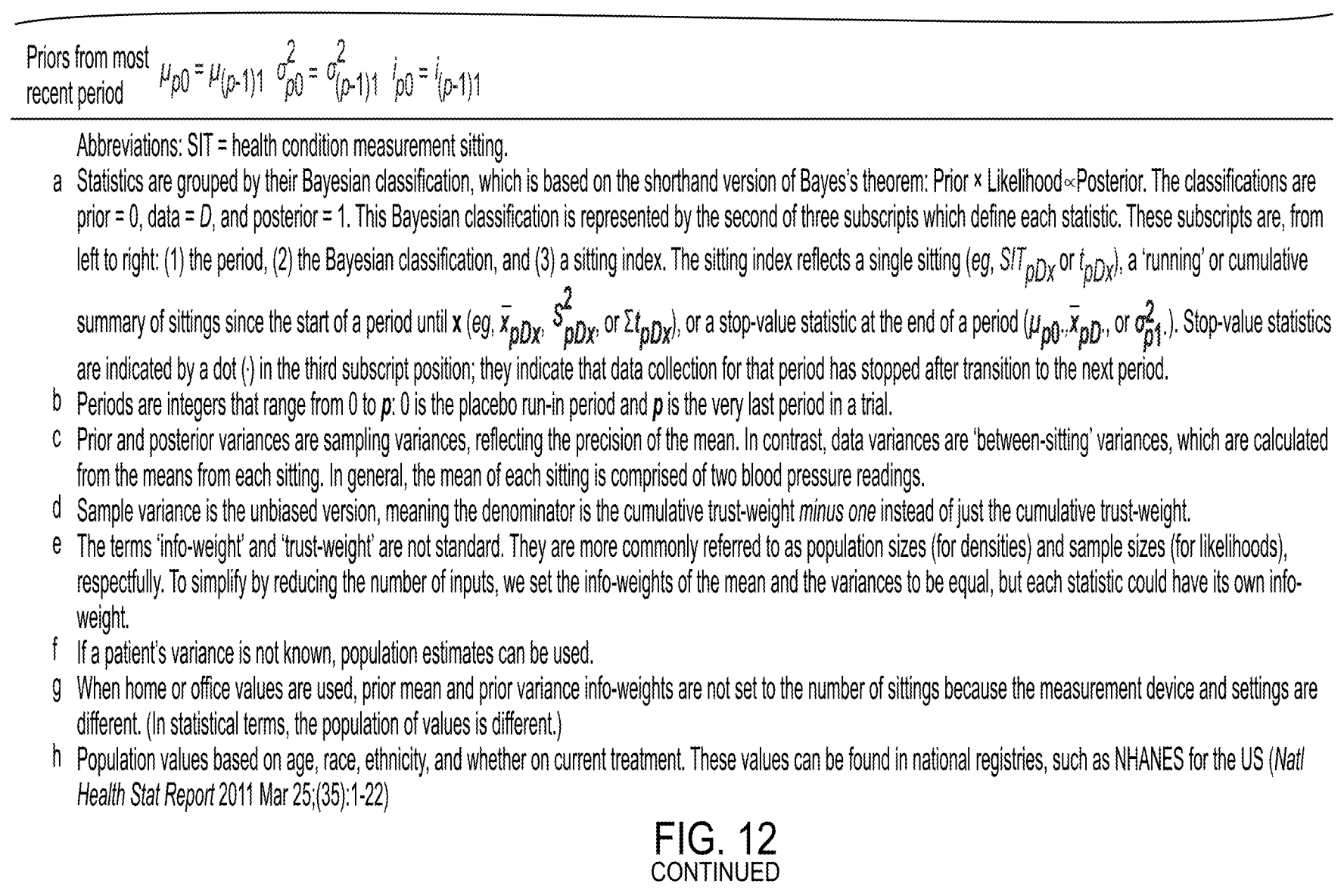

Priors from most recent period $\quad \mu_{p0} = \mu_{(p-1)1} \quad \sigma^2_{p0} = \sigma^2_{(p-1)1} \quad i_{p0} = i_{(p-1)1}$ Abbreviations: SIT = health condition measurement sitting.

a Statistics are grouped by their Bayesian classification, which is based on the shorthand version of Bayes's theorem: Prior x Likelihood∝Posterior. The classifications are prior = 0, data = D, and posterior = 1. This Bayesian classification is represented by the second of three subscripts which define each statistic. These subscripts are, from left to right: (1) the period, (2) the Bayesian classification, and (3) a sitting index. The sitting index reflects a single sitting (eg, $SIT_{pDx}$ or $t_{pDx}$), a 'running' or cumulative summary of sittings since the start of a period until x (eg, $\bar{x}_{pDx}$, $S^2_{pDx}$, or $\Sigma t_{pDx}$), or a stop-value statistic at the end of a period ($\mu_{pD\cdot}$, $\bar{x}_{pD\cdot}$, or $\sigma^2_{p1\cdot}$). Stop-value statistics are indicated by a dot (·) in the third subscript position; they indicate that data collection for that period has stopped after transition to the next period.

b Periods are integers that range from 0 to $p$. 0 is the placebo run-in period and $p$ is the very last period in a trial.

c Prior and posterior variances are sampling variances, reflecting the precision of the mean. In contrast, data variances are 'between-sitting' variances, which are calculated from the means from each sitting. In general, the mean of each sitting is comprised of two blood pressure readings.

d Sample variance is the unbiased version, meaning the denominator is the cumulative trust-weight *minus one* instead of just the cumulative trust-weight.

e The terms 'info-weight' and 'trust-weight' are not standard. They are more commonly referred to as population sizes (for densities) and sample sizes (for likelihoods), respectively. To simplify by reducing the number of inputs, we set the info-weights of the mean and the variances to be equal, but each statistic could have its own info-weight.

f If a patient's variance is not known, population estimates can be used.

g When home or office values are used, prior mean and prior variance info-weights are not set to the number of sittings because the measurement device and settings are different. (In statistical terms, the population of values is different.)

h Population values based on age, race, ethnicity, and whether on current treatment. These values can be found in national registries, such as NHANES for the US (*Natl Health Stat Report* 2011 Mar 25;(35):1-22)

FIG. 12
CONTINUED

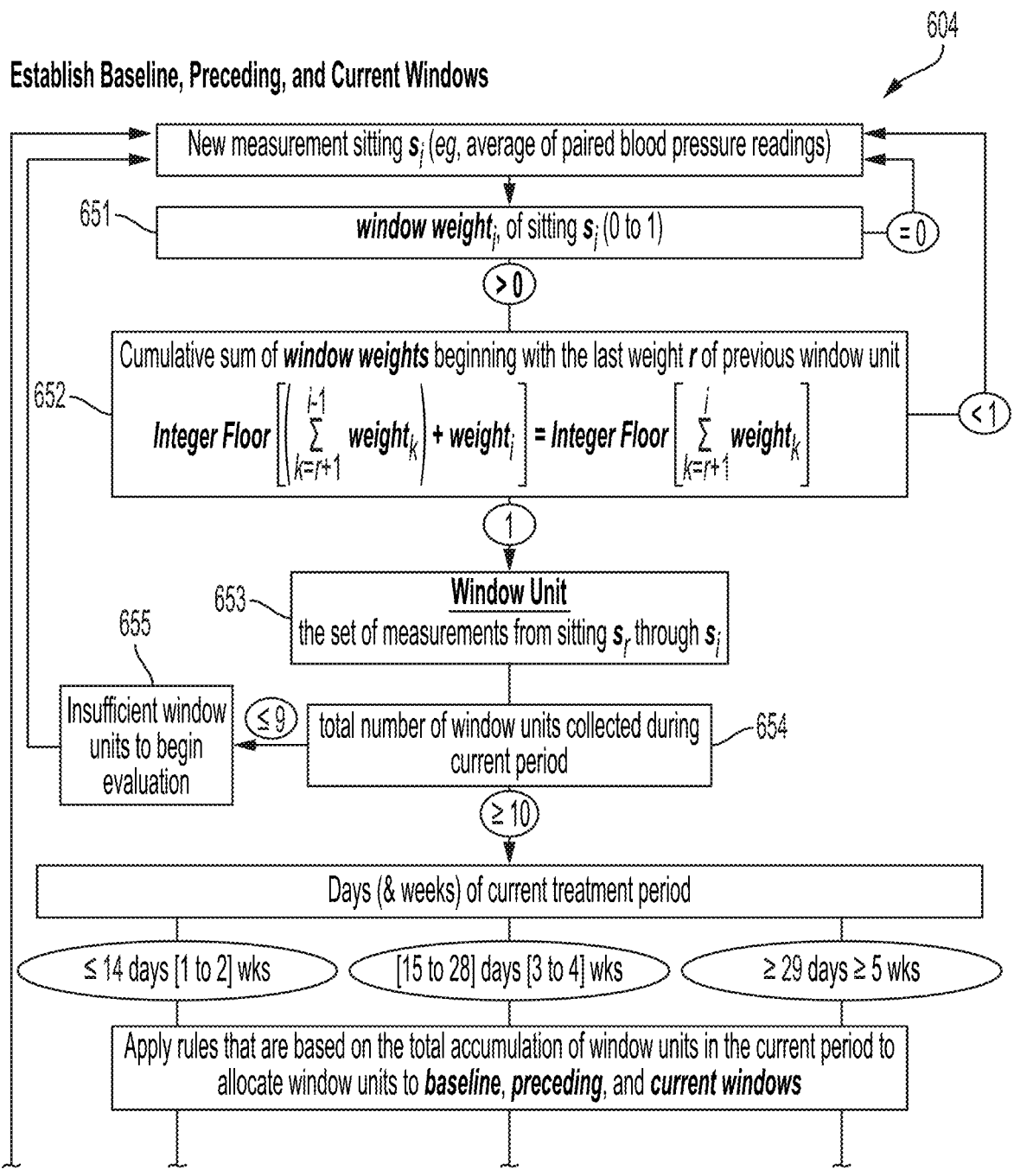

Establish Baseline, Preceding, and Current Windows

604

New measurement sitting $s_j$ (eg, average of paired blood pressure readings)

651 — *window weight$_j$* of sitting $s_j$ (0 to 1) — $= 0$ $> 0$

652 — Cumulative sum of *window weights* beginning with the last weight $r$ of previous window unit $$Integer\ Floor\left[\left(\sum_{k=r+1}^{j-1} weight_k\right) + weight_j\right] = Integer\ Floor\left[\sum_{k=r+1}^{j} weight_k\right]$$

$< 1$ $1$

653 — Window Unit
the set of measurements from sitting $s_r$ through $s_j$

655 — Insufficient window units to begin evaluation — $\le 9$ — total number of window units collected during current period — 654

$\ge 10$

Days (& weeks) of current treatment period $\le 14$ days [1 to 2] wks     [15 to 28] days [3 to 4] wks     $\ge 29$ days $\ge 5$ wks Apply rules that are based on the total accumulation of window units in the current period to allocate window units to *baseline*, *preceding*, and *current windows*

Baseline window any sittings that precede the preceding window; not used to generate priors until 5 window units have accumulated (until then, use the last current window of *p* - 1)

Preceding window sittings from 5 window units that precede the current window

Current window sittings from last 5 window units

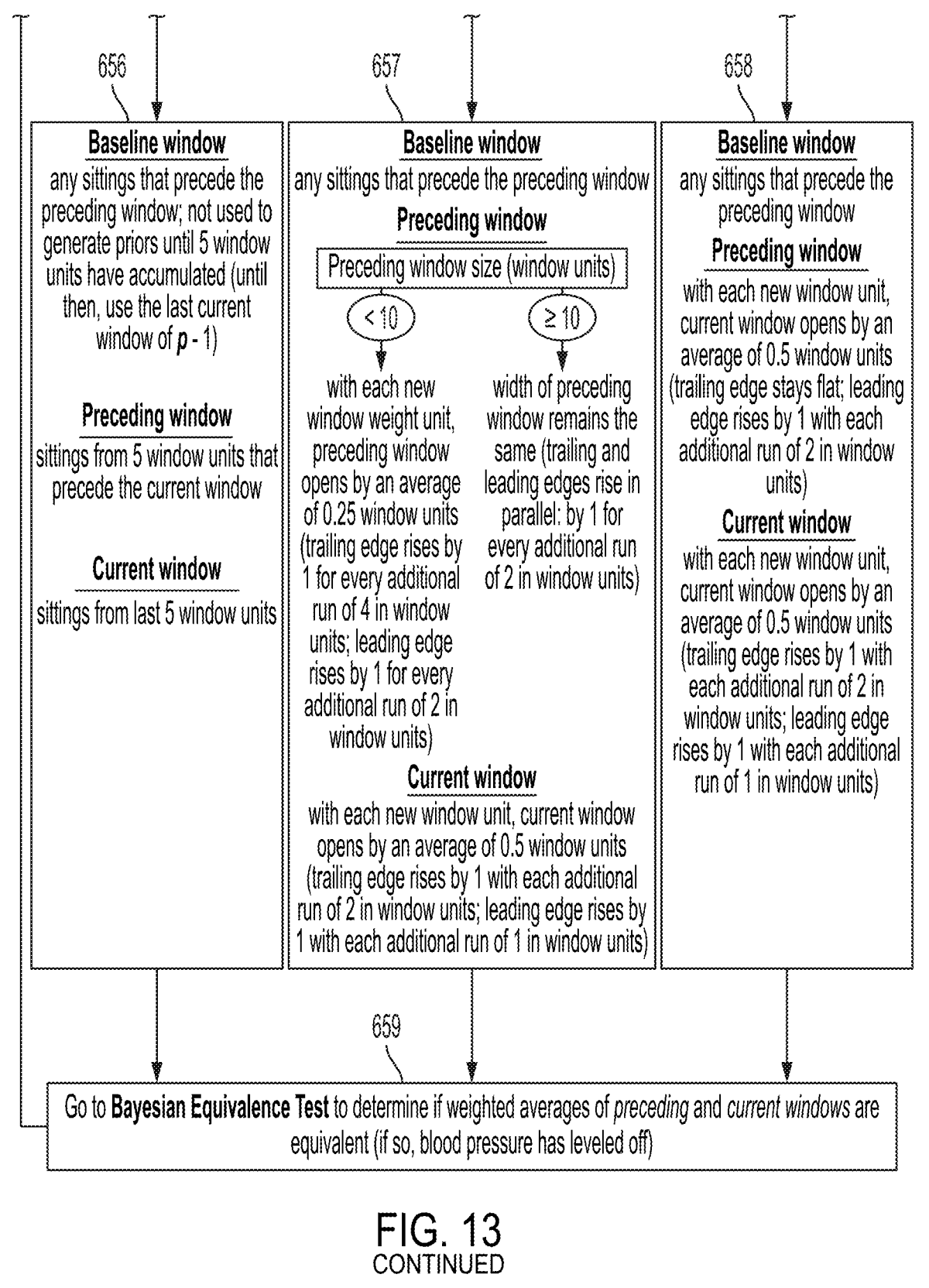

657

Baseline window any sittings that precede the preceding window

Preceding window

Preceding window size (window units)

( < 10 )                    ( ≥ 10 )

with each new window weight unit, preceding window opens by an average of 0.25 window units (trailing edge rises by 1 for every additional run of 4 in window units; leading edge rises by 1 for every additional run of 2 in window units)

width of preceding window remains the same (trailing and leading edges rise in parallel: by 1 for every additional run of 2 in window units)

Current window with each new window unit, current window opens by an average of 0.5 window units (trailing edge rises by 1 with each additional run of 2 in window units; leading edge rises by 1 with each additional run of 1 in window units)

658

Baseline window any sittings that precede the preceding window

Preceding window with each new window unit, current window opens by an average of 0.5 window units (trailing edge stays flat; leading edge rises by 1 with each additional run of 2 in window units)

Current window with each new window unit, current window opens by an average of 0.5 window units (trailing edge rises by 1 with each additional run of 2 in window units; leading edge rises by 1 with each additional run of 1 in window units)

659

Go to Bayesian Equivalence Test to determine if weighted averages of *preceding* and *current windows* are equivalent (if so, blood pressure has leveled off)

FIG. 13
CONTINUED

| Week | Day | Number of cumulative window units | | Baseline Window | | Preceding Window | |
|---|---|---|---|---|---|---|---|
| | | Leading edge | Trailing edge | Leading edge | Trailing edge | Leading edge | Trailing edge |
| — | 1 | — | — | — | — | — | — |
| — | 2 | — | — | — | — | — | — |
| — | 3 | — | — | — | — | — | — |
| — | 4 | — | — | — | — | — | — |
| — | 5 | — | — | — | — | — | — |
| — | 6 | — | — | — | — | — | — |
| — | 7 | — | — | — | — | — | — |
| — | 8 | — | — | — | — | — | — |
| — | 9 | — | — | — | — | — | — |
| 1-2 ≤14 | 10 | 1 | — | 1 | 5 | 6 | 10 |
| 1-2 ≤14 | 11 | 1 | 1 | 2 | 6 | 7 | 11 |
| 1-2 ≤14 | 12 | 1 | 2 | 3 | 7 | 8 | 12 |
| 1-2 ≤14 | 13 | 1 | 3 | 4 | 8 | 9 | 13 |
| 3-4 15-28 | 14 | 1 | 3 | 4 | 8 | 9 | 14 |
| 3-4 15-28 | 15 | 1 | 3 | 4 | 8 | 9 | 15 |
| 3-4 15-28 | 16 | 1 | 3 | 4 | 9 | 10 | 16 |
| 3-4 15-28 | 17 | 1 | 3 | 4 | 9 | 10 | 17 |

Current Window

Evaluation Number: 1 2 3 4 5 6 7 8 9 10 11 12 13 14 15 16 17 18 19 20 21 22 23 24 25 26 27 28 29

FIG. 14

| | | | | | | | | |
|---|---|---|---|---|---|---|---|---|
| 3-4 | 15-28 | 33 | 1 | 7 | 8 | 17 | 18 | 33 |
| 3-4 | 15-28 | 34 | 1 | 8 | 9 | 18 | 19 | 34 |
| 3-4 | 15-28 | 35 | 1 | 8 | 9 | 18 | 19 | 35 |
| 3-4 | 15-28 | 36 | 1 | 9 | 10 | 19 | 20 | 36 |
| 3-4 | 15-28 | 37 | 1 | 9 | 10 | 19 | 20 | 37 |
| 3-4 | 15-28 | 38 | 1 | 10 | 11 | 20 | 21 | 38 |
| 3-4 | 15-28 | 39 | 1 | 10 | 11 | 20 | 21 | 39 |
| 3-4 | 15-28 | 40 | 1 | 11 | 12 | 21 | 22 | 40 |
| 3-4 | 15-28 | 41 | 1 | 11 | 12 | 21 | 22 | 41 |
| -5 | -29 | 42 | 1 | 11 | 12 | 22 | 23 | 42 |
| -5 | -29 | 43 | 1 | 11 | 12 | 22 | 23 | 43 |
| -5 | -29 | 44 | 1 | 11 | 12 | 23 | 24 | 44 |
| -5 | -29 | 45 | 1 | 11 | 12 | 23 | 24 | 45 |
| -5 | -29 | 46 | 1 | 11 | 12 | 24 | 25 | 46 |
| -5 | -29 | 47 | 1 | 11 | 12 | 24 | 25 | 47 |
| -5 | -29 | 48 | 1 | 11 | 12 | 25 | 26 | 48 |
| -5 | -29 | 49 | 1 | 11 | 12 | 25 | 26 | 49 |
| -5 | -29 | 50 | 1 | 11 | 12 | 26 | 27 | 50 |

Preceding window maintains 10 window units

Key:
Baseline window
Preceding window
Current window
\# Enumerated window units

FIG. 14
CONTINUED

SMART DRUG SELECTION AND DISPENSING SYSTEM AND METHOD

PRIORITY

The present invention claims priority to U.S. Provisional Application No. 63/476,827, filed Dec. 22, 2022, the disclosure of which is hereby incorporated by reference its entirety.

BACKGROUND OF THE INVENTION

The present invention relates generally to selecting optimal drug treatments for individuals and, more particularly, to a precision drug dispensing assembly, an integrated cloud-based system of connectedness between users (patients, prescribers, and pharmacies), and an analysis method.

Individual patients often fail to respond to drugs selected from best available evidence. This is because most evidence relies on group averages. But patients are individuals who do not always conform to group averages.

Suppose one group of individuals is prescribed drug A and another group is prescribed drug B. Additionally, suppose that, for whatever chosen outcome, the effects of each drug vary across the individuals within each group, a phenomenon known in the art as individual treatment heterogeneity. So, even if the group given drug A does better on average than the group given drug B, some patients in the drug A group would have done better if they had been given drug B; similarly, some patients in the drug B group would have done worse if they had been given drug A. Just how many patients would have responded differently than their group average will depend upon the properties of drugs A and B, as well as the nature of the patients, themselves, including their genetics, underlying health conditions (comorbidities), and psychology. Front-line prescribers (clinicians who prescribe drugs) intuitively understand that drugs work differently for different patients and that some drugs only work for some people.

Accordingly, there exists a need to help prescribers match their patients to the right drugs to quickly provide safe and effective treatment.

SUMMARY OF THE INVENTION

Embodiments of the present invention comprise a system including a personalized drug dispensing and patient monitoring device with network connectivity (e.g., local network, the Internet, etc.). The system can include a dispensing assembly; a drug reservoir assembly; input and output devices, such as measurement instruments, a display screen, audio input and output, and the like; a cloud-based system to facilitate communication between prescriber-users and pharmacy-users, and software to analyze measurements and carryout a set of prescribed orders in a closed loop fashion.

The dispensing assembly can include a body or housing portion, a chamber where drugs are dispensed into and retrieved, and a container that encloses the drug reservoir assembly. The drug reservoir assembly is a reservoir disc that contains one or more compartments to store and, if desired, conceal drugs; multiple drugs of the same type and dose are stored within each compartment. A central drive of the drug reservoir assembly is operatively connected or registered with a mateable motor of the dispensing assembly such that the reservoirs selectively rotate or index on or about the dispensing assembly. The reservoirs are manipulated to eject the drugs into the dispensing section.

In various embodiments, the dispensing assembly can be prescribed and can arrive with the drug reservoir assembly prefilled with multiple types and dosages of drugs or with the dispensing assembly and reservoir assembly separately provided. The software of the integrated drug selection system (stored in both the cloud system and within the dispensing assembly) implements treatment protocols (outpatient order sets) prescribed by an individual prescriber-user or consistent with professional recommendations, published and accepted methodologies, etc. Various embodiments employ software algorithms and ongoing measurements of patient-user response while short courses of specific drugs and dosages are dispensed. Drug regimens are compared systematically to determine which is most effective and least bothersome to an individual patient-user, for example.

The dispensing assembly can collect, process, and communicate data via wired or wireless (Wi-Fi, Bluetooth, cellular, NFC, etc.) connections from peripheral or like devices, including body weight scales, blood pressure monitoring devices including wrist monitors or cuffs, blood glucose monitors, wearables or removable devices (Apple Watch, Fitbit, smart dental retainers, etc.), implantables (OptiVol, CardioMEMS, smart dental bands or braces), and the like. Data are also obtained periodically from patient-users when they answer, input or enter responses to questionnaires or survey instruments, which may include ratings about symptoms (for example, frequency or the severity) or about how a treatment is otherwise impacting a patient-user, including overall wellbeing, potential side effects, or bothersomeness. This information can be gathered by an app on a device, such as a mobile device (for example, a smartphone, tablet, etc.), a desktop computer, or other computing devices, or entered directly into the system using its keypad or touch screen inputs as well as through voice-controlled technology (like Siri or Alexa). The system can be programmed so that when data includes measurements that fall outside of predetermined ranges, like a blood pressure consistently above a desirable level, an electronic alert or notification can be sent to a clinic, prescriber-user, or the cloud-based platform. The system can also send automatic refill requests to clinics, pharmacies, prescriber-users, or the cloud-based platform when the contents within the drug reservoirs drop below a certain level.

The system collects measurements pertaining to health conditions that measure the effect of the dispensed drug, including physical phenomena like blood pressure or patient reported outcomes like symptoms. The system assigns weights to each measurement, which we refer to as 'trust weights' because they reflect the degree to which measurements accurately reflect the impact of the current drug regimen on the underlying health condition parameters of interest. (For example, if a blood pressure measurement is obtained while a patient-user is not adherent to a drug regimen, then that measurement is not to be 'trusted' to reflect the impact of that drug regimen on that patient's hypertension) The weighted measurements are used in a Bayesian analysis to evaluate the effectiveness of various drug regimens administered throughout implementation of an outpatient order set. The Bayesian analysis determines when response(s) to drug regimens have stabilized, when desired precision about the response(s) have been achieved, and for which drugs are the treatment target(s) attained with the least degree of adverse effects, such as side-effects or bothersomeness.

In accordance with the outpatient order set, the controller operates the system to dispense a drug regimen while obtaining measurements of the patient-user's health condition from one of several potential input devices. Each set of nearly contemporaneous measurements comprising a 'sitting' which, like individual measurements, can be weighted with 'trust weights' that reflect the degree to which measurements accurately reflect the impact of the current drug regimen on the underlying health parameters of interest. The sittings, weighted or not, are then used to generate Bayesian estimates of a patient-user's health condition parameters while taking a particular drug regimen. These estimates are assessed for their stability and precision; if stable, precise, and suggestive that the patient-user is unlikely to achieve a desired treatment target for the health condition of interest with the current drug regimen, the system automatically advances to the next drug regimen, as set out by the outpatient order set.

The outpatient order set can dispense a placebo to assist in the diagnostic assessment and classification of a health condition by establishing the placebo effect for each patient-user. In certain cases, the best drug regimen may not include an active medication. Additionally, after a plurality of drug regimens, the system may conclude that a previously-tested drug regimen, while not meeting the probability threshold for a desired treatment target, may nevertheless be the best possible regimen among those trialed. Similarly, two or more drug regimens may lead to similar estimates of one health condition parameter (such as, in an illustrative embodiment, a reduction in blood pressure) while having dissimilar estimates for another parameter (such as, in an illustrative embodiment, a bothersome side effects); the system may then determine the best drug regimen by incorporating values or preferences of the patient-user, the prescriber-user, or both.

The above summary is not intended to describe each illustrated embodiment, claimed embodiment or implementation of the invention. The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

BRIEF DESCRIPTION OF THE DRAWINGS

The invention may be more completely understood in consideration of the following detailed description of various embodiments of the invention in connection with the accompanying drawings, in which:

FIG. 12 is a table of illustrative statistics of inputs and outcomes for a Bayesian analysis of high blood pressure, which is an illustrative embodiment of the present invention applied to a health condition for which the treatment is monitored by a measurement of numerical continuous data, in this case, blood pressure, and treatment success is evaluated with analytic formulas.

FIG. 13 is a flow diagram of the processing methods for a drug selection system using the illustrative example of high blood pressure for the treatment of hypertension and other specific conditions and particularly, the step of determining if a treatment response has leveled off by establishing baseline, preceding, and current windows in accordance with embodiments of the present invention to generate a Bayesian equivalence test.

DETAILED DESCRIPTION OF THE INVENTION

Figure 1:
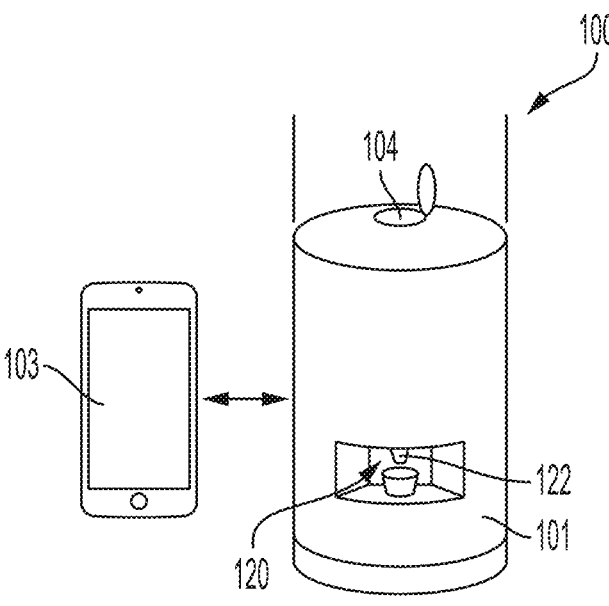
FIG. 1 shows an exemplary drug dispensing assembly, and corresponding sections, assemblies, components, and patient-user devices and peripheral devices thereof, in accordance with embodiments of the present invention.

While the invention is amenable to various modifications and alternative forms, specifics thereof have been shown by way of example in the drawings and will be described in detail. It should be understood, however, that the intention is not to limit the invention to the embodiments described, including the health condition of high blood pressure or any health condition for which the treatment is monitored by a measurement of numerical continuous data. On the contrary, the invention is to cover all modifications, equivalents, and alternatives falling within the spirit and scope of the invention as defined by the appended claims; this includes, but is not limited to, health conditions other than hypertension, including conditions for which drug treatment is monitored by measurements that are numerical and continuous, as well as other conditions that are monitored by measurements that are not numerical and continuous; other measurements include other numerical types, (including, for example, discrete, ratio, interval, etc.), as well as ordinal and nominal measurements.

A primary job of prescribers is to match their patients to the right drugs. For decades it has been understood that the best way to do this is with a 'try-and-see' approach. Various candidate drugs, sometimes in combination, are prescribed for brief durations in sequence until the best regimen is found. In the art, such a process is known as a single patient trial, a single-case trial, N of 1 trial, or a try-and-see trial; we will hereafter refer to these trials as 'try-and-see' trials. While try-and-see trials are the agreed upon gold standard for selecting the right drugs for individual patients, they are cumbersome to implement. Prescribers must switch between candidate drugs as rapidly as possible while monitoring patient response, maintaining 'blindedness,' and objectively compiling summary statistics for ongoing assessment. These tasks are not only time-consuming for both the prescriber and the patient but also prone to error. Lots of know-how and resources are needed to efficiently and safely implement try-and-see trials. The result is that, for many of the chronic health conditions that most prescribers face, drugs are not optimized to individual patient response but selected by default in a one-size-fits-all approach. (For the purposes of the invention described herein, a health condition is any condition that could conceivably be treated or caused by a drug; such conditions are also known as health problems, wellness, health conditions, illnesses, sicknesses, risk factors, diseases, placebo effects, and nocebo effects.)

The invention described herein is designed to make try-and-see trials feasible for a solo prescriber by automating tasks that would otherwise require a dedicated team of nurses, pharmacists, and statisticians. Tasks necessary to implement try-and-see trials can be grouped into three domains: gathering information about a patient's response to a drug regimen, switching between candidate drug regimens to compare them, and processing information about responses to various drug regimens to determine which response is best for an individual patient.

A prescriber desires actionable information about whether a patient is responding to a prescribed drug regimen. This begins with reliable measurements for quantifiable outcomes of interest, such as physical phenomena like blood pressure or patient reported outcomes like symptoms. The invention described herein may utilize automated measurement instruments, including peripheral devices (such as, in an illustrative embodiment, an automated blood pressure cuff) and the base itself (such as, in an illustrative embodiment, a delivery of survey instrument and point-of-care patient entry) to monitor how a given patient-user responds to a drug. Then, to ensure that a patient-user is taking a drug while measurements are being obtained, adherence is tracked by recording the time and date when each pill is retrieved. Lastly, baseline measurements can be collected while administering a placebo to distinguish changes due to the biologic effects of active drugs from changes due to the placebo or nocebo effects of pills.

A prescriber must also be able to safely and efficiently change candidate drug regimens. As described herein, the invention obviates new prescriptions by simply switching dispensing from one reservoir to another. The ordering of drug regimens is predetermined by the prescriber-user upfront, when the outpatient order set is initially prescribed (as further discussed herein below), but a prescriber-user may remotely change the outpatient order set, including the sequence of drug regimens, in response to new information. Patient-users can be kept unaware when a transition between drug regimens occurs because the therapies in the form of pills or capsules that are preloaded into the disc reservoir can be over-encapsulated with opaque gelatin capsules to hide their distinct shapes, colors, and sizes; if such an embodiment is used, each pill is only distinguishable by a coded identifier that is printed on the capsule. In addition, because the disc reservoir can be concealed by an opaque shell, patient-users can remain unaware of which compartment a pill is sourced from and when that compartment changes, further ensuring that patient-users are kept unaware of a drug regimen transition, if desired. Safeguards may be necessary for reducing or eliminating drug-administration errors and for restricting patient-user access to the drugs. Conventional method of patient profiling may generate alerts for unsafe doses, potential allergic reactions, duplicate therapy, contraindications, drug interactions, or other specific drug-related information. Similarly, stocking procedures implemented by the pharmacy-user should be implemented to ensure accuracy of the contained drugs.

To turn measurements that are used to monitor health conditions and obtained during try-and-see trials into decisions about which candidate drugs are likely to work best, a prescriber first determines when each candidate drug regimen has been given enough time to reach its maximal effect. A prescriber then decides if the effect is likely to achieve the desired target response (which includes factoring in any bothersome side effects). Both determinations—first about whether a maximal effect has been reached and then about whether that effect is optimal—are made more difficult by the fact that measurements used to monitor health conditions are often widely variable, even when the health conditions, themselves, appear clinically stable. This variability means that prescribers must incorporate the variability of measurements obtained both before and during various drug regimens to decide if any changes represent real treatment responses or just measurement noise.

Traditionally, at least three different strategies have been used to manage the variability of measurements that are used to monitor health conditions during a drug treatment. One strategy is to calculate a single value from a collection of measurements that is considered typical, such as an average (an arithmetic mean) or median value. While straightforward, simple means or medians have major limitations. A prescriber cannot use them to assess how chance (known as 'sampling variability' by statisticians) may be impacting the relationship between the true status of a patient's health condition and observed measurements of that condition. In statistical terms, the unobservable truth (the 'parameter' representing the current state of a health condition under a drug regimen) can only be estimated by the measurements obtained during a drug regimen (the 'data' observed). An additional statistical tool—a statistical inference—is needed to assess the relationship between the parameter and its estimates.

The second strategy for managing measurement variability uses the most applied method of statistical inference. Often referred to as the traditional or orthodox method, the frequentist method of statistical inference relies on comparing a p-value calculated from a particular set (or 'sample') of measurements against conventional benchmarks (most commonly 0.05). A major problem with the frequentist method is that each time someone (e.g., a prescriber or patient) or something (e.g., a computer driven by an algorithm) having the authority to stop a study 'peeks' at a parameter estimate, the likelihood of making an error (called a 'type 1 error' by statisticians) increases. To adjust for this increase, statistical penalties are imposed that make the conventional benchmarks more stringent.

The exact rules that govern these penalties are complex and difficult to apply in real time, especially for front-line prescribers. The inevitable outcome, however, is that more data (health condition measurements) are required to counteract them. The frequentist method, therefore, disincentivizes prescribers from monitoring their patients' treatment response in real time. This makes the frequentist method untenable in real-world clinical practice because safety concerns (not to mention patients' desire to monitor their own health conditions) demand that treatment response be viewed repeatedly.

The third strategy for managing measurement variably, which is employed by the present invention, is a Bayesian method of statistical inference that does not impose statistical penalties for 'peeking' at parameter estimates. Prior information about the status of a given patient-user's health condition, including whether that patient-user is likely to respond to a particular drug regimen, is combined with measurements obtained while that drug regimen is given. The combined result, known by statisticians as a 'posterior probability distribution', represents the most updated and specific information about the likely impact of a particular drug regimen on an individual patient-user. Traits of this posterior, such as its width ('precision') and relative proportion above or below a target value ('posterior probability'), can be viewed as frequently as needed, even after each additional measurement, without statistical penalty. (The opportunity to stop data collection when a threshold value is reached, often referred to as 'optional stopping rules', may bias a Bayesian analysis because a run of unlikely but possible values may unduly influence a posterior. However, this effect can be counterbalanced by requiring that decisions only be made from narrowly distributed, or precise, posteriors.) Such traits can then be compared against thresholds established by the prescriber-user. In this way, progression through a set of prescribed orders (such as the outpatient order set described herein) can occur automatically, advancing to the next drug regimen when the estimate of the patient-user's response to the current regimen is precise enough but unlikely to be sufficient.

Despite rigorously addressing measurement variability, the benefits of a Bayesian method have not yet been realized in try-and-see trials. This is because the tasks involved, such as the mathematics and the interpretation of the results, are too complex, especially for solo prescribers in routine clinical practice.

The invention described herein, however, can automatically implement a Bayesian analysis for try-and-see trials. It first gathers measurements while switching various candidate drug regimens to achieve a desired precision for health condition parameter estimates. These parameter estimates are compared against prescribed thresholds—both thresholds of precision and effect (the effect being achievement of a desired clinical outcome, or best possible outcome with the least bothersome side effects, that is, a treatment target)—as a set of orders (an outpatient order) is implemented in a closed loop fashion (without real-time prescriber-user approval) until the right drug regimen (the regimen with the highest likelihood of successfully achieving the target response while also being least likely to cause bothersome side-effects) is found for each individual patient-user.

Referring generally to FIGS. 1-16, an integrated drug selection system, a precision drug dispensing assembly, and an analysis method configured to optimize and individualize drug treatment is shown. A drug dispensing assembly, comprised of a reservoir assembly and base, can be included to provide a small and complete unit uniquely configured for personal usage.

Figure 2:
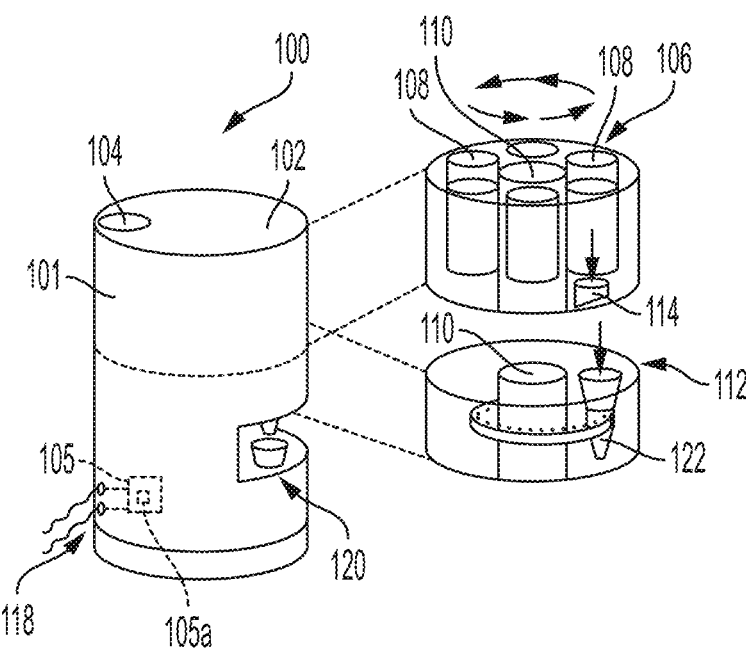
FIG. 2 shows aspects of exemplary drug dispensing assembly, and corresponding sections, assemblies, and components thereof, in accordance with embodiments of the present invention.

Each embodiment of the dispensing assembly 100 can comprise a controller 105 or like electronic hardware that can include a microprocessor 105*a* and physical memory coupled to the microprocessor 105*a* (as shown in FIG. 2). One or more of these dispensing assembly components (including, the controller 105, processor 105*a*, memory, etc.) can be provided with the dispensing assembly and/or the reservoir assembly for embodiments of the dispensing assembly 100. A computer readable program code can be stored in the physical memory (including, without limitation, random access memory, flash memory, or storage drive) of the dispensing assembly base 112*a*. The computer readable program code is configured such that when executed by the processor 105*a*, the code causes the dispensing device to perform the steps and processing of the invention described herein. A communication, storage, and power section can be provided at section 118 of the dispensing assembly base 112*a*. For example, ethernet and USB ports can be included with section 118 and in operative communication with the processor 105*a*. In addition, the dispensing assembly base 112*a* can include network components to facilitate wired and wireless (including, without limitation, Bluetooth, Wi-Fi, cellular, etc.) communication.

Referring to FIGS. 1-6, embodiments of the dispensing assembly 100 can include a main body or housing portion 101. An upper portion of the body 101 can include a fixed drug reservoir assembly 106 (or section or chamber). The fixed reservoir assembly 106 can have a removable lid or top portion 102. The reservoir assembly and/or upper portion of the body 101 can be configured to prevent users from being able to determine which disc compartment is being accessed as treatment therapies, such as drugs in the form of pills are being dispensed; a security mechanism providing such concealment is known in the art as 'blinding' or 'masking'. Concealment may include opaque materials (for body 101 and lid or top portion 102), a locked cover or lockable lid or top portion 102, and additional features that prevent the reservoir assembly from being visible and/or accessible to the user. Additionally, dispensing assembly 100 can include sensors that detect tampering of the lid or top portion 102 to inform the prescriber-user of a potential or actual breach of blinding.

The fixed drug reservoir assembly 106 can include one or more drug reservoirs 108 and a central drive and axis 110. The central drive 110 is operatively connectable and registerable with a motor of the dispensing section 120 such that the reservoirs 108 are capable of selectively rotating about the dispensing section 120. With such embodiments, the reservoirs 108 are large enough for each to contain pills or capsules in bulk or loose form in quantities sufficient to perform the proposed treatment or study. For example, each reservoir can be sized to contain 10-120 pills or capsules.

The drug reservoir assembly can be filled by the user. With other embodiments, the reservoirs 108 are sized and shaped to include or define drug pods. The pods can be prefilled with drug and provided to the patient-user to be placed within a reservoir. In various embodiments, the pods are not separable from and are integrated with, or part of, the reservoirs.

Upon rotation, the reservoirs move to a position above a dispensing chamber in a manner that aligns a reservoir containing the drug currently indicated by the patient order set. The drug within the aligned reservoir 108 is then dispensable through the dispensing assembly base 112. An output dispensing section 120 is also provided and can include a bottom dispensing assembly base 112 for dispensing the drug to a myriad of receiving vessels or devices, such as a cup 124.

Before, during, and after the filling process is complete, software within the processor 105a allows the prescriber-user, or other medical personnel, to monitor and control the insertion of drugs and how those drugs are dispensed. As described further herein, the prescriber-user's instructions (including an outpatient order set, as well as any modifications to that set) can be delivered to the dispensing device via a cloud computing device (including, without limitation, Internet connected), a USB thumb drive, or a device in operative communication with the dispensing assembly 100, controller 105, and processor 105a. The provided instructions enable the dispensing assembly 100 to deliver drug in any specified combination, timing, or other pattern.

Figures 7, 8:
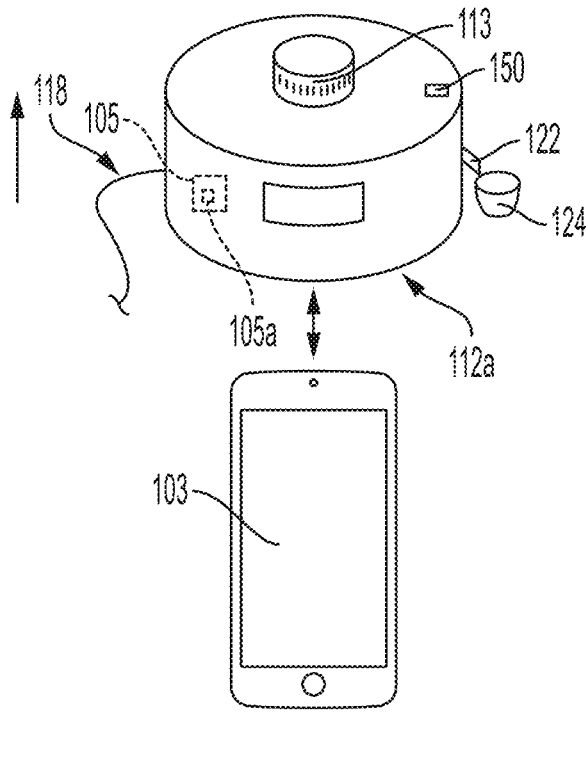
FIG. 7 shows a rotatable drug reservoir assembly and a dispensing assembly for an integrated drug selection system, and corresponding patient-user devices and peripheral devices, in accordance with embodiments of the present invention.
FIG. 8 depicts a rotatable drug reservoir assembly and a dispensing assembly for a drug dispensing assembly, in accordance with an aspect of embodiments of the present invention.

Referring to FIGS. 7 and 8, an embodiment of the dispensing assembly 100 comprising a detachable drug reservoir assembly 106a that is a separable disc, capable of being detached and reattached as needed, and a dispensing assembly base 112a is shown.

The assemblies 106a, 112a can be included with, housed in, or otherwise include any of the devices, mechanisms, housings, structures, body sections, software, and the like disclosed herein for various embodiments. The detachable reservoir assembly 106a can include one or more drug reservoirs 108a and a central drive or axis 110. The drug reservoirs 108a extend through the detachable reservoir assembly 106a to define bottom outlets 108b. The central drive section 110 is operatively connected or registered with a mateable drive element and motor 113 of the dispensing assembly base 112a such that the reservoirs 108a selectively rotate on or about the dispensing assembly base 112a. In other embodiments, the dispensing assembly base 112a can selectively rotate about the reservoirs 108a.

The spinning rotation of the detachable reservoir assembly 106a correspondingly aligns a reservoir 108a and a corresponding bottom outlet 108b with a top inlet 150 of the dispensing assembly base 112a. As such, one or more pills P, capsules, and the like, can drop or otherwise travel from the bottom outlet 108b of the detachable reservoir assembly 106a, and into the top inlet 150 of the dispensing assembly base 112a, for dispensing through the dispenser 122. The assemblies 106a, 112a are adapted to snap or otherwise couple together such that the reservoir assembly 106a rotates relative to the dispensing assembly base 112a. Further, the detachable reservoir assembly 106a, or portions thereof, can be disposable in various embodiments and can be preloaded with customized drug regimens, including over-encapsulated drug, and delivered to the patient-user for use with the dispensing assembly 100.

The dispensing assembly base 112a can include the computing processor 105a and connectivity hardware (including, without limitation, Bluetooth, Wi-Fi, ethernet, USB, cellular, etc.) and can pair and communicate with other computing devices 103, such as mobile devices (including, without limitation, smartphones, tablets, etc.), desktop computers, and other devices and peripherals, such as blood pressure cuffs, body weight scales, wearables, etc. The processor 105a is operatively connected and in communication with the one or both of the assemblies 106a, 112a, and the components, mechanisms, and devices thereof, such that the processor 105a can control the spinning upper disc 106a and track each mechanical step in the capsule or drug dispensing process. The processor 105a can be controlled by software that contains detailed order sets that enable ongoing patient-user assessment and drug adjustments. Accordingly, the software and connectivity of the integrated system 900 enable ongoing data exchange with prescriber-users and the cloud-based platform 170. New detachable reservoir assembly discs 106a can be sent to the user patient-user for coupling to the dispensing assembly 100 with new drugs, new drug dosages, and the like. The monitoring and tracking of the dispensing assembly 100 and its software and processor 105a, as well as the software and analysis methods stored in the cloud-based platform 170, provide accurate, responsive, and customizable drug regimens.

Figures 3, 4:
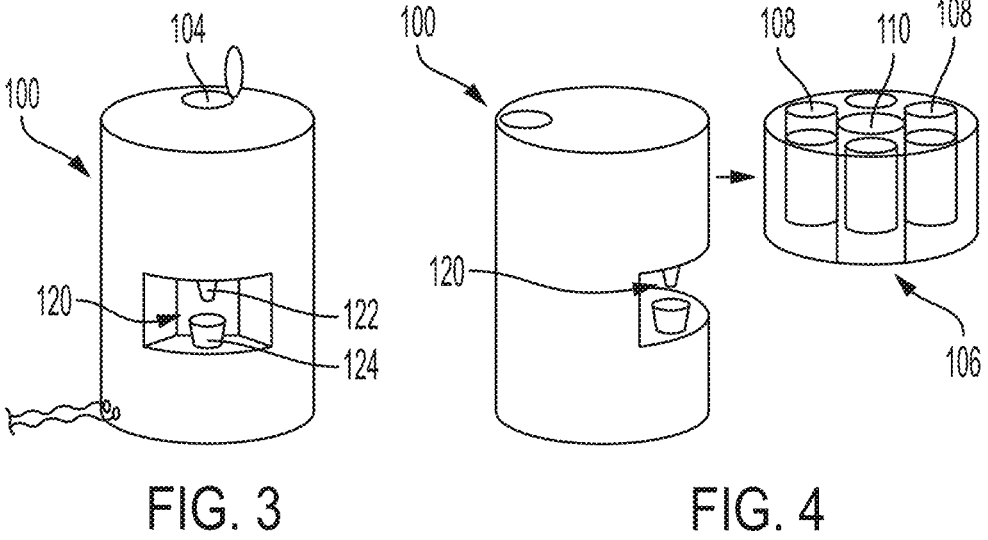
FIG. 3 depicts aspects of exemplary drug dispensing assembly, and corresponding sections, assemblies, and components thereof, in accordance with embodiments of the present invention.
FIG. 4 shows aspects of exemplary drug dispensing assembly, and corresponding sections, assemblies, and components thereof, in accordance with embodiments of the present invention.
Figures 5, 6:
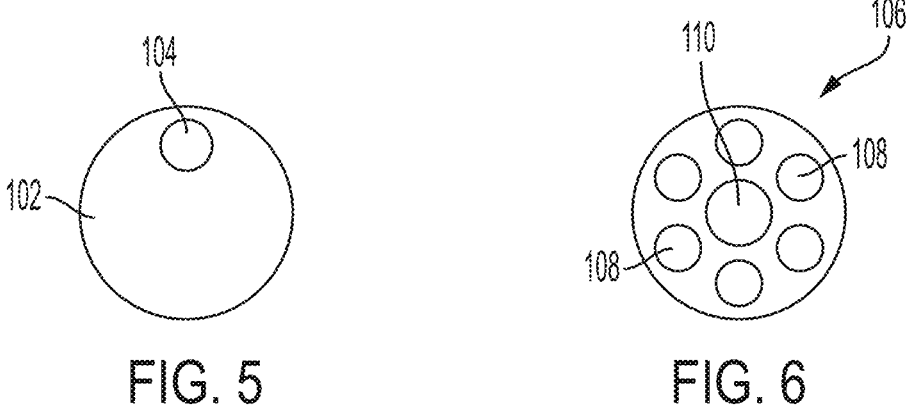
FIG. 5 depicts aspects of exemplary drug dispensing assembly, and corresponding sections, assemblies, and components thereof, in accordance with embodiments of the present invention.
FIG. 6 shows aspects of exemplary drug dispensing assembly, and corresponding sections, assemblies, and components thereof, in accordance with embodiments of the present invention.
Figure 9:
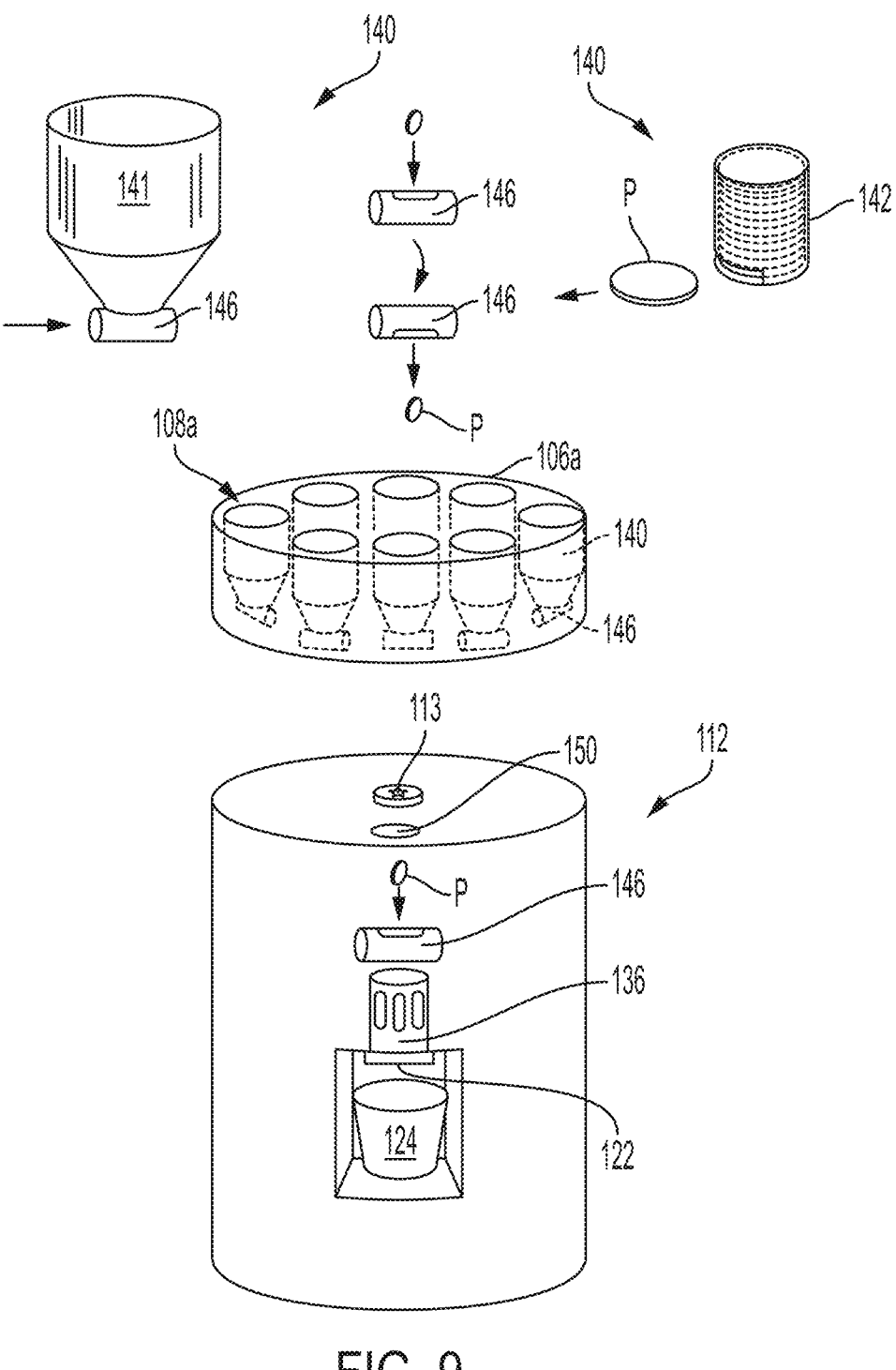
FIG. 9 shows an exemplary dispensing assembly where drugs pass from the reservoir disc section to the dispensing section they go through various sensors for identification and verification.

The bottom of each of the reservoirs 108 or 108a (as shown in FIGS. 4 and 8) can include a bar-code, electromagnetic code, or other identifying indicia or elements, and the dispensing assembly base 112 or 112a (as shown in FIGS. 2 and 7) can include a sensor, reader mechanism or device, etc., to read or sense the unique signature or identification characteristic of the individual reservoirs 108 or 108a. When the dispensing assembly reads or detects the unique signature for the reservoir 108 or 108a containing the correct or desired pills or capsules, the reservoir assembly 106 or 106a (as shown in FIGS. 6 and 8) is rotated into position for dispensing from that reservoir 108 or 108a. Referring to FIG. 9, the reservoirs 108 and 108a can include a rotating element 146 to ensure the drug dispensed from the corresponding reservoir is of the intended dose. Once dispensed, one or more pills or capsules P drop or otherwise exit from the reservoir 108 or 108a (as also shown in FIGS. 4 and 8) through the cavity opening 150 and into a second rotating device element 146, which ensures that a correct number of pills or capsules has been dispensed. Such an embodiment with dual rotating elements 146 as shown in FIG. 9 can increase the level of redundancy and safety provided and can facilitate medication confirmation with the identification of the unique signature or identification characteristic of the individual reservoir 108 or 108a.

Alternative embodiments of a mechanism for dispensing drugs in the form of pills or capsules are contemplated in the dispensing assembly 100, as shown in FIG. 9. The medication reservoirs 108 and 108a can each or separately include or define medication pods 140 that can be reservoirs 108 and 108a (as previously shown) or provided as cartridges 141 containing loose pills, liquid or powder, or magazines 142 containing stacked pills or capsules that can be individually ejected for dispensing. The reservoirs 108 and 108a are sized and shaped to hold one or more, capsules, pills, tablets, and the like. With certain applications, the reservoirs 108a can be sized and shaped to contain a single standardized pod that contains medication in a solid, liquid or powder form or in which a medication cartridge 141 or magazine 142 can be inserted. The pods 140, cartridges 141, or magazines 142 can be prefilled with medication and provided to the patient with the reservoir or shipped separately thereby allowing the patient to insert them into the reservoirs 108 and 108*a*. Alternatively, the drugs in the form of pills or capsules can be preloaded into a reservoir 108 that is adapted to accept blister packs of pills or capsules that can be individually released and dispensed.

The drugs in the form of pills or capsules P fall or otherwise through cavity opening 150, to a dispensing chamber 136 and can be adapted to contain the pills or capsules until the patient-user (or their established surrogate) identifies themselves. Alternatively, the dispensing of a drug can be initiated following patient-user identification. This identification can occur with one or more identification technologies, such as typed or spoken passwords or PINs, facial recognition, retinal scanning, digital fingerprinting, etc. Once the patient-user or surrogate is identified, the dispensing chamber releases the drug which pass through the dispenser 122 and out to the patient-user—for example, in an illustrative embodiment, received into the cup 124. Again, detection, processing, and storage of this dispensing data, such as the time and date the drug was dispensed, is facilitated by the processor 105*a* and stored at the dispensing assembly 100 or via the cloud-based platform for the purposes of increasing the integrity of the collected data.

Figure 10:
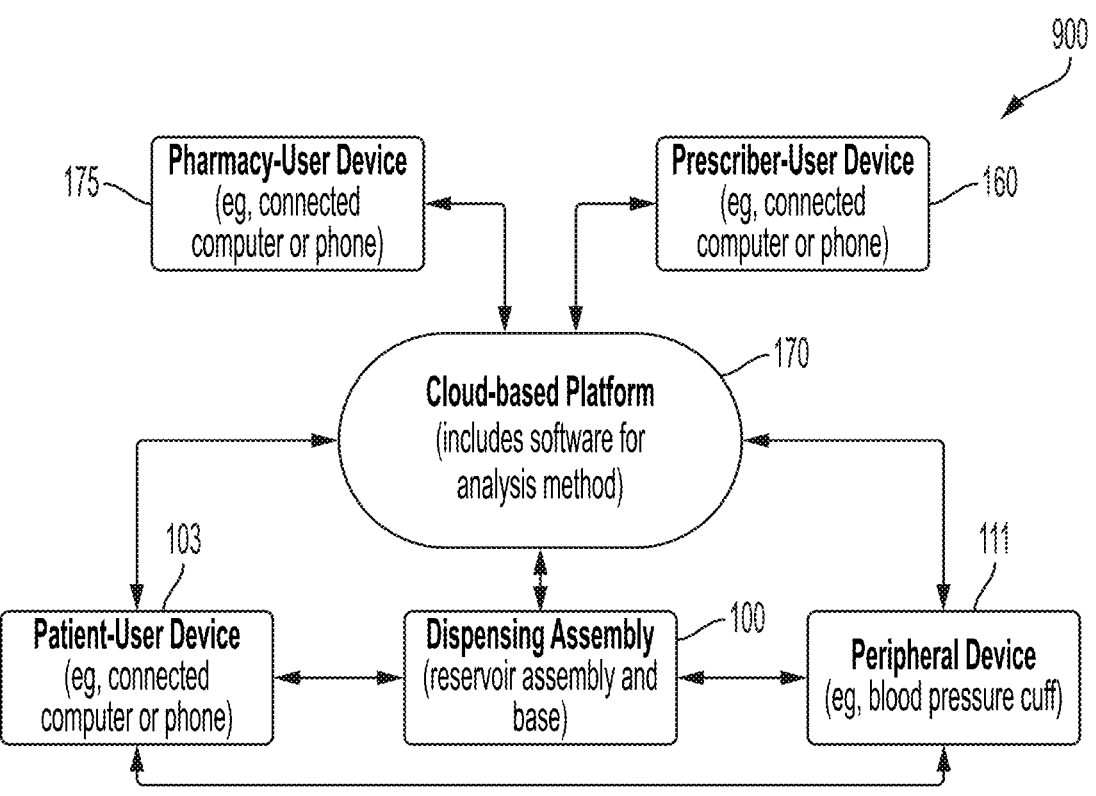
FIG. 10 is a diagram of a hardware and device communication architecture for use with, and including, an integrated drug selection system, in accordance with embodiments of the present invention.
Figure 11:
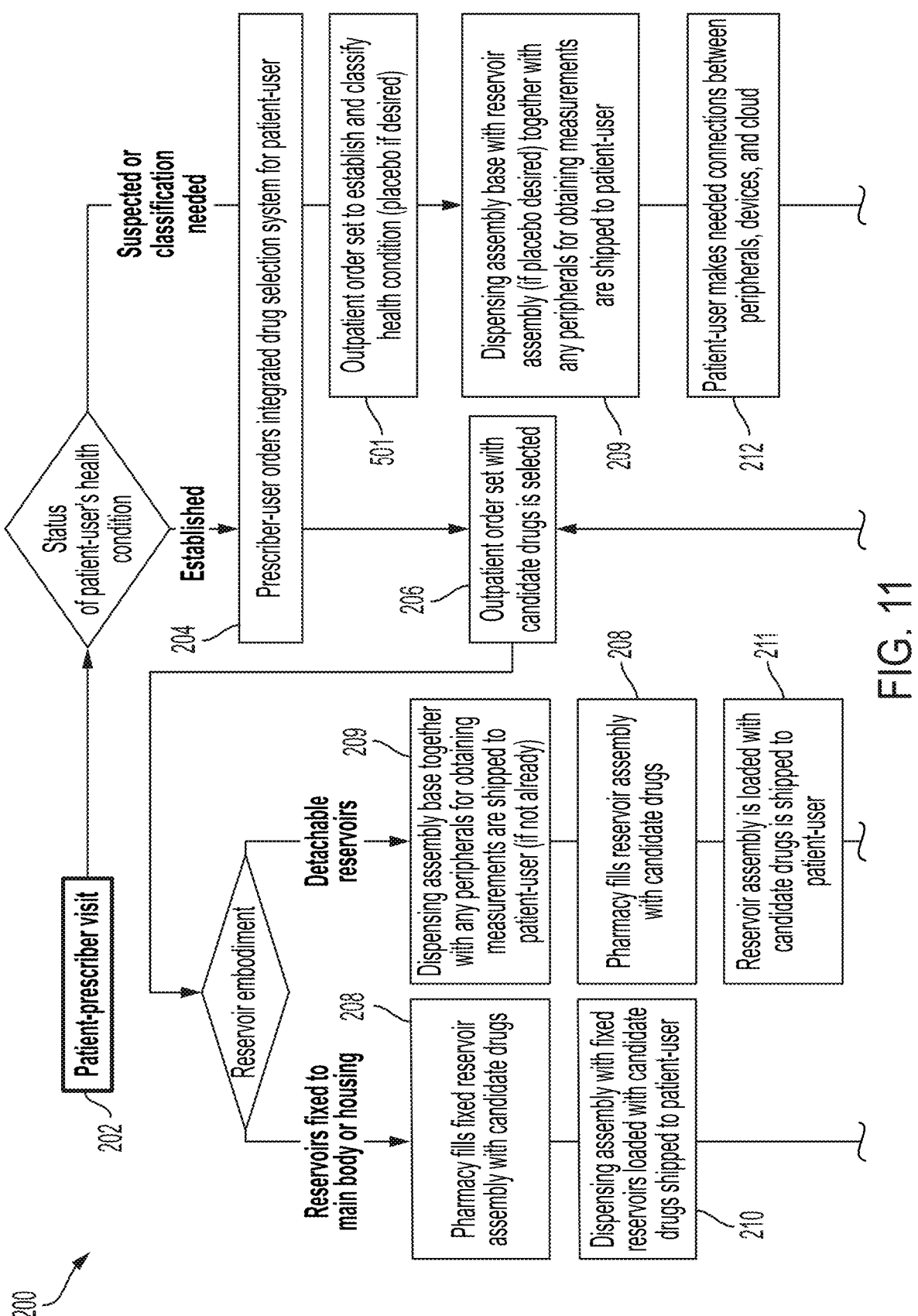
FIG. 11 is a flow diagram showing an exemplary method of use and operation for an integrated drug drug selection system, in accordance with embodiments of the present invention.

Referring to FIGS. 10 and 11, embodiments of the architecture and dispensing methodology for the integrated system 900 are provided. These communication, interaction, and treatment processes and elements can be applied to or incorporated with, in whole or in part, any of the embodiments, aspects, components, devices, and methods of the present invention.

The exemplary architecture of FIG. 10 provides for operative communication between the dispensing assembly 100 and the cloud-based platform 170, the patient-user devices 103, and the peripheral devices 111 (the patient-user devices 103 and the peripheral devices 111 comprising input devices to provide health condition measurements). The exemplary architecture of FIG. 10 also provides for operative communication between the cloud-based platform 170 and a pharmacy-user 175, and the prescriber-user devices 160 The cloud-based platform 170 can provide portal access for prescriber-users (including their staff), patient-users, pharmacy-users, etc., as well as facilitate and control dispensing, data storage, data analysis and processing, treatment processing, and communication between the prescriber-user device 160, the patient-user device 103, and the dispensing assembly 100, as described herein.

As detailed herein, the dispensing assembly 100 is an interactive tool that connects, via a cloud-based platform 170, a prescriber-user (including, without limitation, at prescriber-user device 160) with a patient-user in their home or remote location. The dispensing assembly 100 also interacts with peripheral devices 111, can process data, prompt, and receive input at patient-user devices 103. The system can use ethernet, Wi-Fi, cellular, or any other form of wired or wireless connectivity to receive instructions, directly or indirectly, from the prescriber-user device 160. If Internet connectivity is not available, one or more USB ports (or other data transfer and communication ports) can facilitate the delivery of instructions—for example, by a thumb drive, a computing device, or similar storage or data communication devices.

The peripheral devices 111 can include body weight scales, blood pressure monitoring devices including wrist monitors or cuffs, blood glucose monitors, wearables or removable devices (Apple Watch, Fitbit, smart dental retainers, etc.), implantables (Opti Vol, CardioMEMS, smart dental bands or braces), and a myriad of other health, measurement, and monitoring devices. In certain embodiments, communication with these distinct devices 111 and systems can be accomplished via Bluetooth or wireless network connectivity. This allows input of patient-user measurements and data which are then transmitted to the cloud-based platform 170.

The dispensing assembly 100 also tracks drug adherence and records the effect of treatment, through patient-user devices or peripheral devices. Each time a drug is dispensed, the drug name, dose, and time of day are processed and stored in a log or database. Periodically, the patient-user device 103 or the dispensing assembly 100 itself can prompt the patient-user to answer, via inputs, a symptom questionnaire or to make a physical measurement. For example, blood pressure or body weight data can be received from the operatively coupled peripheral device 111, or from manually inputted data and information including side effects or subjective levels of discomfort. The results are transmitted and stored in a database log—for example, at the patient-user device 103, the controller 105, and/or the cloud-based platform 170.

The patient-user device 103 allows the patient-user to receive prompts and messages either from the cloud-based platform 170 directly, or indirectly through the dispensing assembly 100, while also permitting the patient-user to input data and otherwise interact with the cloud-based platform 170 or the dispensing assembly 100. Patient-user devices 103 can be imbedded with the body 101 of the dispensing assembly or include mobile devices such as smart phones and tablet devices, laptops, personal computers, or any other computing device capable of communicating with the dispensing assembly 100 (including, without limitation, via wired or wireless connectivity), the cloud-based platform 170, and peripheral devices 111.

The prescriber-user device 160 can be in operative communication with the dispensing assembly 100 or the patient-user device 103 through the cloud-based platform 170. Prescriber-user devices 160 can include mobile devices such as smart phones and tablet devices, laptops, personal computers, or any other computing device capable of communicating with the cloud-based platform 170 (including, without limitation, via wired or wireless connectivity). Further, the prescriber-user devices 160, and the patient-user devices 103, can communicate with and process data and execute software code through or via the cloud-based network computing system 170, such as a cloud server, in certain embodiments of the integrated system 900.

Further, the body 101, or other assemblies and sections of the dispensing assembly 100, can include an LCD or like display that displays text and images and facilitates touchscreen inputs. A microphone input and speaker output device can be included to allow for the transmission of audible information from and to the patient-user.

FIG. 11 provides a flow diagram of the method 200 of operating the integrated system 900 in accordance with embodiments of the present invention. The method 200 can be used for diagnosis, classification, or drug treatment of any chronic health condition (including health conditions that are caused by drug treatments) upon which multiple drug or medicinal treatments are available, including, without limitation, hypertension, depression, pain management, acne, addiction (including alcohol-use, tobacco-use, opioid-use disorders) attention deficit hyperactivity disorder, AIDS/HIV, allergies, angina, anxiety, arthritis, asthma, bipolar disorder, bronchitis, cancer, cholesterol, chronic kidney disease, constipation, chronic obstructive pulmonary disease, dementia, diabetes, diarrhea, dizziness, dysuria, eczema, erectile disfunction, fatigue, fibromyalgia, gastroesophageal reflux, heartburn, gout, hair loss, hay fever, headaches, heart disease, heart failure, herpes, hypothyroidism, inflammatory bowel disease, incontinence, insomnia, loss of libido, menopause, mental health, migraines, muscle aches, nausea, neuropathy, obesity, osteoarthritis, osteoporosis, pain, pneumonia, prostate disease, psoriasis, rheumatoid arthritis, schizophrenia, seizures, sexual disfunction, tinnitus, and body weight gain/loss. Similarly, the method 200 can be used for diagnosis of health conditions that are caused by drugs, such as placebo or nocebo effects.

First, at step 202, the patient-user visits their prescriber-user (or other medical personnel). The prescriber-user then, at step 204, orders the integrated drug selection system 900, including the dispensing assembly 100, via a web portal or other interface with the cloud-based platform 170. If the health condition is not yet established but merely suspected or in need of further classification, the prescriber-user selects from the cloud-based platform 170 an outpatient order set to establish and/or classify the health condition at step 501. The dispensing assembly base, the reservoir assembly, and any peripherals needed for obtaining measurements are shipped to or otherwise provided to the patient-user at step 209. At step 212, if necessary, the patient-user can set up the dispensing assembly 100, any patient-user devices 103, and peripherals 111 which are in operative communication with both the dispensing assembly 100 and, via a web portal or other interface, the cloud-based platform 170. At step 218, to determine whether or not the health condition is established, and to further classify it, dispensing assembly 100 implements the outpatient order set and receives patient-user data (including, without limitation, measurements) from patient-user devices 103 and peripheral devices 111 and transmits the data to the cloud. At step 219, the cloud-based platform 170 conducts an evaluation and analyzes the patient-user data to estimate the health condition parameters of interest. Information can be passed to patient-users, prescriber-users, and pharmacy-users.

If the status of a patient-user's health condition is both established and classified as needing treatment at step 239, then the prescriber-user prescribes an outpatient order set with candidate drugs at step 206. The outpatient order set is an ordered list of drugs and corresponding dosages that is consistent with established clinical data and treatment protocols. The prescriber-user can choose from a menu of order sets.

Once the outpatient order set 206 is chosen or inputted, a pharmacy (such as a compounding pharmacy) can be instructed to fill the reservoirs with the prescribed candidate drug(s) consistent with the outpatient order set. The pharmacy personnel can be in operative communication with the cloud-based platform 170 through a pharmacy-user device 175. The pharmacy-user and the prescriber-user can also send, receive, process, and disseminate information and data to each other through the cloud-based platform.

At step 208, the pharmacy fills the reservoirs (108 or 108a) of the reservoir assembly (106 or 106a) with the prescribed drug, either the detachable 106a or fixed reservoir assembly 106, depending on the reservoir embodiment. If the detachable reservoir assembly 106a is used, the filled reservoir assembly is then shipped to the patient-user at step

211 along with the dispensing assembly base 112a; the detachable reservoir assembly is then mated with the dispensing assembly base 112a in step 220. If the fixed reservoir assembly 106 is used, the main body is then shipped to the patient-user at step 210.

All of the reservoirs 108a in the detachable reservoir assembly 106a can be filled with drug, or one or more of the reservoirs 108a can be left empty. The treatment protocol and the corresponding duration for that protocol will be the determining factors. In one prescribed treatment example, the detachable reservoir assembly 106a is filled for a one-month run, and only two or three reservoirs 108a include a drug or a placebo (depending on the protocol prescribed for the try-and-see trial). The other reservoirs 108a (including, without limitation, six or seven reservoirs) can be filled with the patient-user's other prescribed drugs for the patient-user's other health conditions (health conditions that are not affected by the drugs in the try-and-see trial), such as drugs for cholesterol, reflux, diabetes, etc. This inclusion of multiple distinct drugs within the detachable reservoir assembly 106a is facilitated by the prescriber-user. The prescriber-user, via the cloud-based platform 170, can have the patient-user's other drug prescriptions transferred to the relevant pharmacy-user device 175. Accordingly, a new detachable reservoir assembly 106a can be shipped to the patient-user on a regular schedule, such as every month, filled with the appropriate drug from the treatment protocol as well as refills of the patient's other drugs. It is noted that the cloud-based platform 170 and/or the personnel and company controlling and facilitating the processes described herein, can act as the pharmacy for filling and distribution of the reservoirs discs 106a and can monitor, process, and control each aspect of the processes after the initial prescriber-user visit and prescription steps. The reservoir assembly (either the fixed assembly 106 or the detachable reservoir assembly 106a) can be filled with enough drug to run a treatment protocol for a fixed period of time-such as, for example, up to three months.

Operation and use instructions are provided at step 213, for example, how to connect the dispensing assembly 100 to the cloud-based platform 170 via a wireless or wired connection, and how to connect one or more peripheral devices 111. If this is the initial shipment and receipt of the dispensing assembly 100, the patient-user can set up the assembly, components, and any peripherals 111. If the patient-user already has at least the dispensing assembly base 112a of the dispensing assembly 100, the patient-user simply connects the detachable reservoir assembly 106a to the dispensing assembly base 112a for use.

The patient-user then begins the prescribed outpatient order set through the dispensing assembly 100 at step 214. The dispensing assembly 100 receives inputs and data, controls dispensing, monitors adherence, and can provide notifications and operatively communicate data and feedback to the patient-user device 103 as well as the cloud-based platform 170 and the prescriber-user device 160 (step 218). Drugs are dispensed from the dispensing assembly 100 each day (or the prescribed frequency) while the patient-user measures and inputs their health measurements via peripheral devices 111. The patient-user can also input answers to a series of symptom questions through the patient-user device 103 or directly at the dispensing assembly 100—including, without limitation, via a touch input device provided with the dispensing assembly base 112a.

The drugs dispensed correspond to the outpatient order set 206 and the dispensing assembly advances in the outpatient order set 206 based on the analysis of data collected by the patient-user devices 103 and peripheral devices 111. The data are used in a Bayesian analysis (described herein) to determine if a patient-user's health condition parameters of interest, based on measurements obtained, have achieved treatment targets without bothersome side effects. If health condition parameters are not likely to be achieve treatment targets (including side effects), then a change will be automatically implemented, changing the dose or the drug to the next pill in the outpatient order set 206

The treatment change will be seamless and undetectable by the patient-user and does not require further inputs from the patient-user or their prescriber-user. The cloud-based platform 170 provides notification of the change in treatment and the reason for the change (including, without limitation, poor response or side effect) to the prescriber-user. Also, when drug refills are due, the cloud-based platform 170 provides the pharmacy with up-to-date details of the drugs dispensed and the progression of the protocol, through the pharmacy-user device 175. This allows the pharmacy to adapt to the patient-user's unique spot in the protocol and, accordingly, fill and ship a new reservoir assembly (106 or 106a) that contains the drugs and dosages that are required or might be required as the treatment protocol continues. The patient-user will then receive the disc assembly and, in the case of the detachable reservoir assembly 106a, connect the assembly 106a to the dispensing assembly base 112a for another period (including, without limitation, one month) of ongoing use. Ultimately, a drug regimen is selected from the outpatient order set 206 at step 225 when a target response with minimal side effects is attained.

The software 200 also performs ongoing statistical analysis of data inputs from the patient-user. The software 200 can be executed with the processor 105a of the dispensing assembly itself, at the cloud-based platform 170, or at the user device 103. For example, as a try-and-see trial proceeds, the Bayesian posterior probabilities of health condition parameters, which estimate the true underlying patient-user's response to a drug regimen, will be updated. These updated posteriors can be used to determine the probabilities that a given drug regimen will achieve desired treatment targets for a given patient-user and the probabilities that the responses achieved by different drug regimens are meaningfully different from each other.

The following defined terms may be used, and for clarification, they are to be inferred as follows:

health measurement sitting A statistic representing a health measurement from one or more measurements obtained during a discrete period of time when the patient-user's health condition ought to be stable. (For example, if the health condition is blood pressure, the blood pressure sitting is a mean value of paired blood pressure readings when a patient-user is seated and rested. This value is different than the average ambulatory blood pressure, which is an average of many blood pressure readings obtained during routine daytime and nighttime activities.)

dispensed vs retrieved pill At a prescribed time, the systems 100, 103, 160 described herein, dispense pills or capsules into dispensing chamber 136. A patient-user (or a surrogate patient-user) can then confirm their identify for the pills or capsules to be dispensed and retrievable. Once their identify is confirmed, the dispensing chamber allows the pills or capsules to pass into a retrieval chamber 124; when and if a patient-user retrieves pills or capsules from the retrieval chamber, then a timestamp for that retrieval can be recorded.

try-and-see period The duration (typically measured in days) which a drug regimen is applied to determine if a drug regimen is effective at achieving a target. Each period is indexed by its prescribed order in a try-and-see trial.

try-and-see trial The set of try-and-see periods in which a patient-user retrieved at least one dose of the prescribed drug regimen. The trial begins with the first retrieved pill (active or placebo) of the first period and ends with the last retrieved pill (active or placebo) of the last period. Therefore, try-and-see periods that were prescribed but never started are not part of the try-and-see trial.

outpatient order set A prescribed protocol used to implement a try-and-see trial. A protocol includes multiple diagnostic and treatment steps that are guided by branching logic. For example, if patient-user response equals X, administer drug regimen A; whereas if patient-user response equals Y, administer drug regimen B. The details of each step, as well as safety conditions that detail when prescriber-user input is required, are established up front by the prescriber-user.

placebo period A period when an inert placebo is given without active drug. This period typically occurs at the beginning of a try-and-see trial and is, therefore, labeled with a 0 subscript ($p_0$).

active period A period when an active drug regimen is given. The first active drug regimen is labeled $p_1$. Thereafter each unique drug regimen is assigned a new period. For example, if a low dose of a drug that is given during period 4 ($p_4$) is later increased to a moderate dose, then a new active period ($p_5$) begins.

closed loop advancement A feature of each step in an outpatient order set that allows for advancement to a subsequent step without real-time approval from the prescriber-user. Because the prescriber-user establishes the set of conditions required for advancement upfront at the time the prescription was written, approval has, in effect, already been given as long as those conditions are met. Such conditions may include achievement of a desired probability threshold that a patient-user's health condition parameters of interest have achieved a target without the current regimen being too bothersome to the patient-user. This feature can be toggled on or off for each step as desired weight subscripts Weights for health condition measurements are indexed by a left-to-right convention: period p, day i of period p, and health condition measurement sitting k of day i. For example, trust weight 4,3,2 (abbreviated $WTRUST_{4,3,2}$) refers to the $2^{nd}$ health condition measurement sitting on day three of period four. When referring to a cumulative sum of the weights across multiple measurement sittings, instead of a weight for a single sitting, a "c" prefix is used. The range of measurement sitting weights included in the cumulative sum are indicated by the subscript. For example, $cWTRUST_{4,1,1\ to\ 4,14,2}$ refers to the cumulative sum of weights from the first health condition measurement sitting on day 1 of period 4 through the second sitting on day 14 of period 4.

statistics subscripts Each statistic is indexed by 3 subscripts. Below is an example of a probability density for measurement of a health condition known to follow a Gaussian (or normal) distribution, such as blood pressure measurements for the health condition of hypertension, represented by a mean and variance.

$$\mu|\sigma^2 \sim N(\mu_{p0}., \sigma^2_{p0}/i_{p0})$$

These subscripts represent, from left to right: (1) the period, (2) the Bayesian classification, and (3) the health condition measurement sitting index. The first subscript, the period, is an integer from 0 to p; 0 is the placebo run-in period and p is an enumerated period in a trial. The second subscript, the Bayesian classification, is derived from the shorthand version of Bayes's theorem: Prior×Likelihood-∝Posterior. The classifications are prior=0, data=D, and posterior=1. The third subscript, the health condition measurement sitting index, indicates the source of the statistic. Depending upon the statistic being indexed, a sitting index represents either a single sitting (including, without limitation, $SIT_{pDx}$ or $t_{pDx}$) or a cumulative ('running') summary of sittings from the start of a period until sitting x (including, without limitation, $$\bar{x}_{pDx},\ S^2_{pDx},\ \text{or}\ \sum t_{pDx}).$$

If the sitting index is a dot (•), then the statistic is 'closed': it represents a completed period where transition to the next period has already occurred (including, without limitation, $$\mu_{p0.},\ \bar{x}_{pD.},\ \text{or}\ \sigma^2_{p1.}).$$

The following describes various aspects of the integrated system 900, computing devices or assemblies 100, 103, 160 and the software and methods 200 in an illustrative embodiment for diagnosis and treatment of a health condition. In this illustrative embodiment, we consider the health condition of high blood pressure, or hypertension. In this case, the health condition measurement is blood pressure and the peripheral device 111 includes a blood pressure measuring device or instrument.

Hypertension is chosen as an illustrative embodiment because of its familiarity. Any health condition which is effectively treated with drugs and measured in some way to estimate health condition parameters could use the same integrated system, devices, or assemblies to determine the probabilities that a given patient-user's health condition parameters will achieve desired targets. This includes health conditions with measurements that are numerical continuous (like blood pressure), as well as health conditions with measurements that are numerical discrete, interval, ratio, ordinal, or nominal.

In the software and methods 200 of the present invention, Bayesian methods continuously update multiple probabilities related to a patient-user's parameter (in this example, blood pressure) throughout period p. These include, given the measurements obtained during period p, a) the probability that the parameter lowering effect of period p drug(s) has stabilized, b) the probability that the patient-user's parameter while taking period p drug(s) is within a narrow range, and c) the probability that the patient-user is likely to achieve a target parameter while taking period p drugs.

These probabilities can be used to guide the implementation of an outpatient order set. Outpatient order sets are comprised of multiple decision nodes, or branch points, where new information (in this example, blood pressure measurements obtained while taking period p drug(s)) is weighed against threshold conditions (including, without limitation, the probability of achieving a target treatment effect) that were established by a prescriber-user upfront (at the time the order set was prescribed) to determine what steps, if any, should be carried out next.

There are various assumptions, parameterizations, prior probability distributions, mathematical formulas, and methods of approximation for the posterior probability distributions of the health care parameters of interest that could be incorporated into the present invention based on computational ease, the types of health parameters being estimated, as well as patient-user- and prescriber-user preferences. For example, explicit formulas (also known in the art as analytic solutions) are readily available to describe the posterior probability distributions for the mean and variance of blood pressure (FIG. 12). The current invention allows for other methods of approximating posterior probability distributions; such methods are required to estimate multiple parameters at once (joint posterior probability distributions). They include grid-based methods, variational Bayes, Laplacian estimation, and simulation-based (stochastic) methods, such as those based on Markov Chain Monte Carlo methods. As an illustrative embodiment of an analytic solution, the following defaults can be provided for blood pressure; these can be adjusted and customized, as desired, by the prescriber-user and/or the company controlling and facilitating the processes. Alternatively, if computational resources can be used, a simulation-based method could also be selected instead of one based on analytic solutions.

Assumptions We could assume that blood pressure data are normally distributed with the following joint conjugate prior probability densities. Here the statistics listed in parentheses follow usual conventions. The normal probability density is, therefore, represented by the mean and variance, while the inverse gamma probability by the shape and scale.

$$\mu|\sigma^2 \sim N(\mu_{p0.},\ \sigma^2_{p0.}/i_{p0})$$

$$\sigma^2 \sim \text{inverse gamma}(i_{p0.}/2,\ (\sigma^2_{p0.} \times i_{p0.})/2)$$

Note a unique feature of this notation. As is typically known in the art, the probability density for $\sigma^2$ is represented with the inverse gamma probability density. When the probability density of $\sigma^2$ is specified by an inverse gamma probability density, it is equivalent to an inverse chi-squared probability density.

The joint prior probability density can be depicted in the following way:

$$N\text{-}Inv\text{-gamma}\left(\mu,\ \sigma^2|\mu_{p0.},\ \frac{\sigma^2_{p0.}}{i_{p0.}};\ \frac{i_{p0.}}{2},\ \frac{(\sigma^2_{p0.} \times i_{p0.})}{2}\right).$$

A normal likelihood can then be derived from the data acquired during a particular period:

$$(\sigma^2)^{-t_{pD.}/2} \exp\left(-\frac{1}{2\sigma^2}\left[(t_{pD.}-1)S^2_{pD.}+t_{pD.}(\bar{x}_{pD.}-\mu)^2\right]\right)$$

The joint prior probability density and the likelihood are multiplied to generate a joint posterior probability density for the mean and the variance given the data, which can be described as:

$$p(\mu,\ \sigma^2|y) = N\text{-}Inv\text{-gamma}\left(\mu,\ \sigma^2|\mu_{p1.},\ \frac{\sigma^2_{p1.}}{i_{p1.}};\ \frac{i_{p1.}}{2},\ \frac{(\sigma^2_{p1.} \times i_{p1.})}{2}\right)$$

A simulation-based sampling method, as is known in the art, such as those based on a Monte Carlo Markov Chains (or MCMC methods), can be used to generate the marginal posterior probability densities of $\mu$ and $\sigma^2$. Such sampling methods use software to repeat a sampling process thousands of times: first sampling the variance from the joint posterior probability distribution, then using that sampled variance to sample the mean from the joint posterior probability distribution. While such methods require more computational power, the main benefit of such methods is that they do not need to make certain assumptions about the true underlying health condition parameters, such as, in the case of blood pressure, the variance of the true blood pressures for a particular period is equal to the variance of the sample of blood pressure measurements.

Inputs and Outcomes In most settings, the main challenge of using Bayesian methods (instead of traditional methods) is choosing the inputs, or a process called establishing the priors. Priors are a set of educated best-guesses for what the parameters are before data are acquired. In our case, however, priors for a given patient-user's parameters are easily obtained.

As shown in FIG. 12, using high blood pressure analyzed with an analytic solution as an illustrative embodiment, priors for the placebo run-in period can come from at least three different sources: a patient-user's own medical record, a presumed classification or diagnosis of a health condition (for example, stage 1 hypertension), or from a published average population value. During the run-in placebo period (as herein defined above) the selected prior is combined with measurements to generate a posterior probability that is a summary statistic that represents an estimate of the patient-user's health condition parameters; in this case, 'true' average systolic and diastolic blood pressures, as well as side-effects or other subjective patient-reported outcomes, while taking a placebo. These parameters, estimated while the patient-user was taking a placebo, can then serve as a baseline for comparison when the patient-user later is given various active treatments.

Once the estimates of the health condition parameters of interest reach the desired level of precision, then an outpatient order set can transition automatically to the next period. In an illustrative embodiment of high blood pressure, a prescriber-user may select a range of 4 mm Hg, for example, as a clinically relevant degree of precision. And so, once the posterior probability distributions for average systolic and diastolic blood pressures are narrowed enough so that, for example, 95% of the probability distributions, which may be known in the art as 95% credibility intervals, are both within that range, the desired level of precision has been achieved. The posterior of the run-in placebo period then becomes the prior of the first treatment period.

For each subsequent treatment period thereafter the placebo run-in period (see FIG. 16), the priors used for the analysis of that period are chosen by the prescriber-user, as incorporated into the outpatient order set. Priors can be, for example, the posterior from the run-in period (which can be conceived as a patient-user's baseline parameter) or the posterior from the most recent or relevant treatment period. For example, if the drug regimen for period p is a moderate dose of drug A, the default priors would be posteriors from the period with a low dose of drug A. On the other hand, if the drug regimen for period p is a low dose of drug B, which the patient-user has not yet been exposed to, the default priors would be posteriors from the run-in placebo period. In this way, relevant priors specific to both the blood pressure response of the patient-user, as well as the preferences of the provider-user, are easily and defensibly selected, thereby overcoming the main challenge to using Bayesian methods: the establishment of priors.

Info-Weights or Precision The analytic method depicted in FIG. 12 allows for explicitly considered info-weights, which are also known in the art as measures of precision. In other embodiments that use non-analytic methods of approximating posterior probability distributions (such as with simulation-based or stochastic methods), info-weights are implicitly represented by the narrowness (precision) of the prior probability distribution. Info-weights and precision reflect the weight (or relevance) of information about a patient-user's heath condition parameters of interest before new measurements are obtained; in other words, info-weights and precision represent the shape (narrowness) of the prior probability distributions of an individual patient-user's heath condition parameters in a particular try-and-see period (as herein defined above). Information used for prior distributions is either obtained within the try-and-see trial (as herein defined above), including, without limitation, the variance of measurement sittings during the placebo period or external to the try-and-see trial, including, without limitation, an average within-person variance of measurement sittings published in the literature for patient-users matched on age, sex, and gender. Information will generally be weighted more (info-weights will be higher or prior probability distributions will be narrower or more precise) when information is obtained within, rather than external to, a try-and-see trial. In both cases—whether prior information is represented by an explicit info-weight or implicitly by the shape of a probability distribution—the end-result is the same: the estimates of health care parameters (represented by posterior probability distributions) are 'info-weighted' because they incorporate information about the prior probability into the eventual estimates of the parameters.

Referring to FIG. 11, embodiments of the dispensing assembly 100 can include pre-filled reservoirs with over-encapsulated drugs loaded therein-including, without limitation, at a remote or separate location, prior to delivery to a patient-user. The drugs can be dispensed from the device by rotating the reservoirs, or from each reservoir position absent rotation. This embodiment can include the method and software 200 adapted to treat specific conditions-including, without limitation, hypertension and a myriad of other health conditions or issues.

The software and methods 200 will enable drugs to be dispensed in a manner that personalizes and optimizes the treatment. Treatment targets (or goals) can be set according to the consensus recommendations of accepted experts, boards, and panels. In the case of hypertension, such recommendations include those from the American College of Cardiology (ACC) and the American Heart Association (AHA). In addition to try-and-see trials, the algorithms and processing of the software 200 can include sequential monotherapy, stepped care, stepwise dose adjustment patterns, and other treatment protocols and techniques.

As illustrated in the flow chart of FIG. 11, the method and software 200 of the integrated system 900 can provide treatment protocols consistent with recommendations and published methodology-again, provided by the ACC, AHA, and the like. At step 501 the Placebo Run-In procedure is preferably performed to establish a health condition and classify its severity, as described in FIG. 15. Optionally, if the prescriber-user determines the risks associated with the use of a placebo are unacceptable, treatment can proceed without the placebo period.

Figure 15:
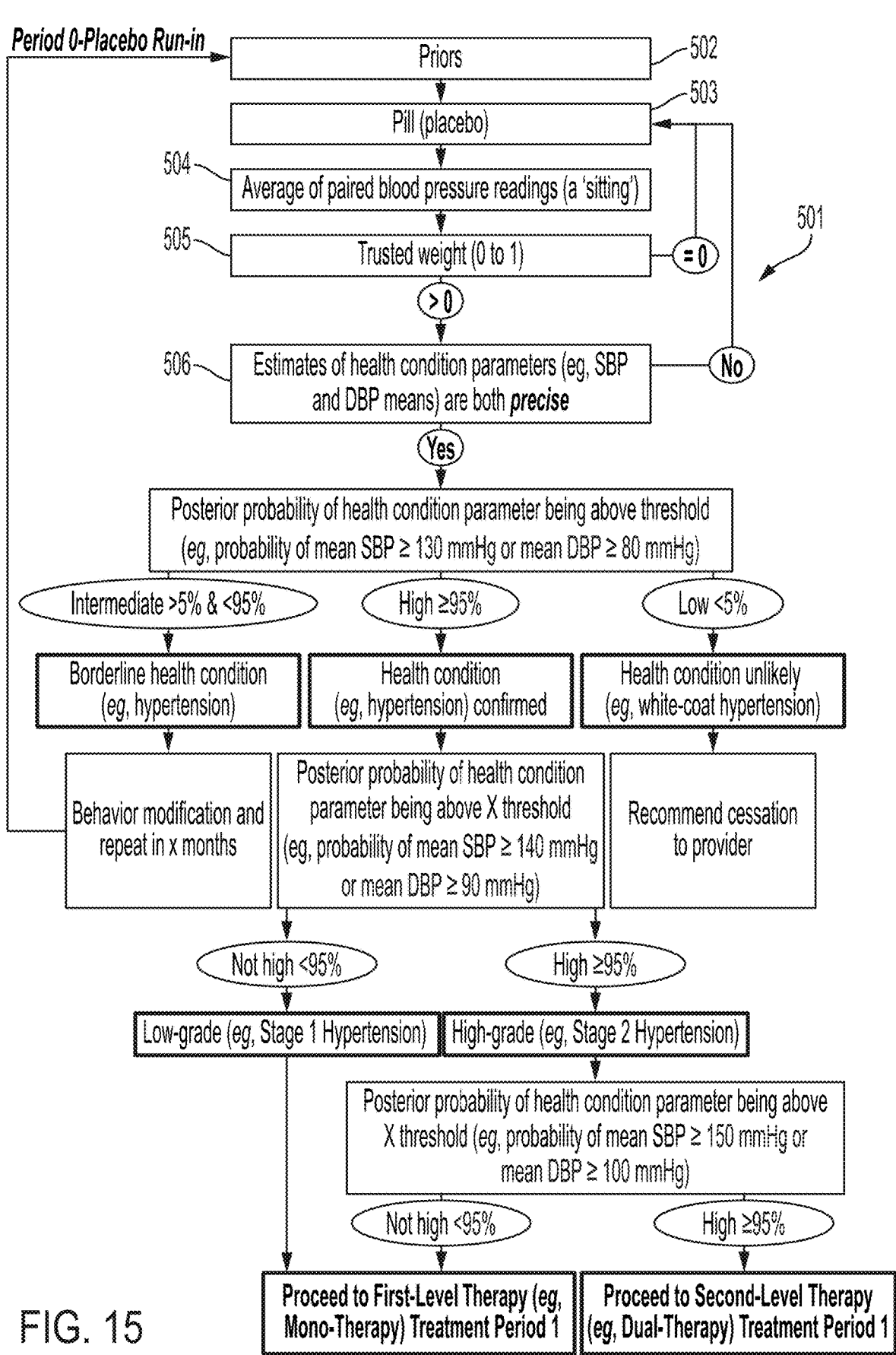
FIG. 15 is a flow diagram of the processing methods for a drug selection system for the step of performing a placebo run-in to confirm and classify a health condition (in this illustrative example, high blood pressure) in accordance with embodiments of the present invention.

Referring to FIG. 15, the process for performing a placebo run-in procedure is provided, if the clinician determines the risk of running a placebo run-in is acceptable. The placebo run-in phase in this illustrative embodiment is used to diagnose hypertension (for example, distinguish true from white-coat hypertension) and, if present, classify its severity. First, priors are chosen at step 502 by the prescriber-user based on available data and current belief. The prescriber-user may believe, for example, that a patient-user has stage 1 hypertension, meaning that the patient-user likely has true hypertension (not white-coat hypertension) and that the severity of the hypertension is stage 1. The prior probability distribution of the systolic blood pressure could then be set to a mean of 134.5 mm Hg and an age-specific variance (obtained from population distributions found in the literature). Other prior probability distributions can be selected from a menu of options or customized by the prescriber-user.

Once the priors are established a placebo is dispensed daily from the output 120 at placebo therapy step 503. At least one reservoir must be prefilled with a placebo. Two placebos can be dispensed when the prescriber-user suspects high-grade stage 2 hypertension requiring dual, or two-pill, therapy. Each day one or more paired blood pressure readings (referred to as a blood pressure 'sitting') is obtained by the patient-user using the peripheral device 111 and averaged to generate a daily blood pressure reading at step 504. Safeguards can be included to provide an electronic alert or notification that can be sent to a clinic, prescriber-user, or the cloud-based platform if sittings include data measurements that fall outside of predetermined ranges, for example, if blood pressure is consistently above a threshold level.

Each health condition measurement sitting is 'trust-weighted' at step 505. Not all measurement sittings (and the measurements that comprise those sittings) should be valued equally. Trust weights are used to de-emphasize measurements that have low likelihood of reflecting the effects of drug(s) that are actively prescribed upon the health condition parameters.

Trust weights are comprised of four component weights: carryover, ramp up, adherence, and measurement weights. The magnitude of a trust weight ranges in value from 0 (no trust) to 1 (full trust) and reflects the degree to which a measurement sitting is expected to reflect the activity of the current drugs on the health parameters of interest. The trust weight for an individual k measurement sitting on day i of period p is the sum of four component weights for that measurement sitting divided by 4 (the number of component weights).

$$WTRUST_{p,i,k} =$$

$$\frac{a_p WOVER_{p,i,k} + b_p WRAMP_{p,i,k} + c_p WAD_{p,i,k} + d_p WMEAS_{p,i,k}}{4}$$

The cumulative trust weight (distinguished by the "c" prefix) is the sum of trust weights for a range of measurement sittings. The range of measurement sittings in the notation below are from health measurement sitting u on day y in period t to sitting j on day h in period g.

$$cWTRUST_{t,y,u \ to \ g,h,j} =$$

$$\sum_{p=t,i=y,k=u}^{g,h,j} \left( \frac{a_p WOVER_{p,i,k} + b_p WRAMP_{p,i,k} + c_p WAD_{p,i,k} + d_p WMEAS_{p,i,k}}{4} \right)$$

The constants $a_p$, $b_p$, $c_p$, and $d_p$ add to 4. They allow the relative importance of each component weight of the trust weight to vary by period and, if desired, by the prescriber-user and/or patient-user.

While trust weights are applied during the analysis, they require that the drug dispensing assembly timestamps when a) pill(s) are retrieved and b) measurements are obtained, as herein described above with reference to devices or assemblies 100, 103, 160.

The 4 separate components of a trust weight are derived from pharmacology and metrology (the science of measurement), as depicted below.

Carryover weight A patient-user's health condition parameter during the initial days of period p will be affected in part by the drug regimen taken during p−1, the previous period. The magnitude and duration of these carryover effects will depend upon a) how consistently and for how long p−1 drug(s) were taken at the end of p−1 and b) how quickly the effect(s) of p−1 drug(s) upon health condition parameters are lost upon cessation (the 'off-rates'). This weight reflects the waning carryover effects of the drug(s) given during the previous period (p−1); and so, this weight begins at or near 0 at the beginning of a period, when carryover effects are high, and increases to 1 as those effects wane. The shorthand label is $WOVER_{p,i,k}$, which stands for Weight due to carryOVER for sitting k on day i of period p; the carryover weight is specific to each period, day, and sitting. This weight depends upon the off-rate(s) of the drug(s) given during the most recent period (p−1). If the dose of a drug given during p−1 was lower than the dose of the same drug given during p, the carryover effect of the drug will be ignored during p ($WOVER_{p,i,k}$ will be set to 1); in addition, WRAMP will be weighted higher because the rate of onset will be more rapid.

Ramp up weight It will take time for a drug regimen to achieve its maximal effect(s) on health condition parameters. The degree to which the maximal effect is achieved is largely dependent on a) how long a drug regimen has been taken and b) how quickly the effect(s) of p drug(s) upon health condition parameters are gained (the 'on-rates'). This weight reflects the waxing activity of the drug(s) as a drug regimen is being initiated and has only achieved a portion of its maximal potential; and so, this weight begins at or near 0 at the beginning of a period, when potential activity is low, and increases to 1 as potential activity maxes out over time. The shorthand label is $WRAMP_{p,i,k}$, which stands for Weight due to RAMP up for sitting k on day i of period p. This weight depends upon the on-rate(s) of the drug(s) at the doses given during p; the ramp up weight is specific to each period, day, and sitting.

Adherence weight The effect(s) of a drug regimen upon health condition parameters will wax and wane with interruptions, such as those dues to nonadherence. Both the 'off-rates' and 'on-rates' will determine the activity: the off-rate will determine the rate of loss of activity while the on-rates will determine how quickly the activity is regained. This weight reflects both the waxing and waning activity of period p drug(s) due to interruptions of a period prescription. When there are no interruptions, the weight will be 1. However, after interruptions from, for example, non-adherence (which is determined by, for example, the timing of drug retrieval, as recorded by the dispensing assembly 100), the activity of the drug(s) decreases, and the weight is correspondingly less than 1. The shorthand label is $WAD_p$, $_{i,k}$, which stands for Weight due to ADherence for sitting k on day i of period p. This weight depends not only upon both the on- and off-rates of the period p drugs, but also upon previous patterns of adherence. For example, the $WAD_{p,i,k}$ after a single day of non-adherence will be higher if that day followed a week of perfect adherence versus a week of infrequent, sporadic adherence. The adherence weight is specific to each period, day, and sitting.

Measurement weight Rather than reflect the pharmacologic properties of the prescribed drug(s), this weight reflects the quality of the measurements obtained during a measurement sitting. The shorthand label is $WMEAS_{p,i,k}$, which stands for Weight due to MEASurement for sitting k on day i of period p. This weight depends upon a) how many measurements were obtained during a sitting (the target amount for blood pressure, for example, is two), b) the timing of the measurement sitting in a day (as recorded by the dispensing assembly 100, the patient-user devices 103, or the peripherals 111) if, for example, the measurement follows a diurnal pattern, and c) whether the patient-user followed a prescribed protocol, such as, in the case of blood pressure sittings, remaining still for 5 minutes, obtaining measurements from the same arm, and/or receiving assistance from a caregiver. The measurement weight is specific to each period, day, and sitting.

Still in reference to FIG. 15, measurements from each trust-weighted sitting with trust weight >0 is compiled at step 506, along with the prior probability distribution, to generate posterior probability distributions for whatever health condition parameters are of interest; in this illustrative embodiment, the parameters are systolic blood pressure and diastolic blood pressure.

If posterior probability distributions are precise enough (meaning that the posterior probability distributions of relevant health condition parameters are narrow enough for the preferences of the prescriber-user), compiled health condition parameter estimates are compared against important clinical thresholds. The location and spread of these parameter estimates (which are depicted as posterior probability distributions) can be used to establish a health condition (including, without limitation, borderline hypertension, true hypertension, or white-coat hypertension) as well as a classification of severity of that condition (like, stage 1 or stage 2). For example, if a patient-user's mean systolic blood pressure has a 98% probability of being greater than 130 mm Hg, a 96% probability of being greater than 140 mm Hg, but less than a 95% probability of being greater than 150 mmHg, then that may indicate the patient-user has stage 2 hypertension. Default clinical thresholds (such as 130 mm Hg in the above example) can be guideline-driven but can also be customized by the prescriber-user. Thresholds for probability distributions (typically, a common threshold for 'high' probability is ≥ 95%) can also be customized.

Parameter estimates generated during the placebo period (including, without limitation, blood pressure means and standard deviations) can be used later in try-and-see trials for establishing priors relevant to a patient-user. Similarly, measurements that reflect the bothersome effects of a drug obtained from the devices, peripherals, or assemblies 100, 103, 111, 160 described herein that both tracks adherence and collects symptom feedback, can be used for comparative purposes.

To achieve a desired level of precision for a patient-user's health condition parameter while taking a particular drug regimen, prescriber-users can select one of four strategies. The first three strategies entail changing the measurement regimen of period p by: 1) extending the duration of period p; 2) increasing the frequency of measurement sittings within period p; or 3) extending the duration of period p and increasing the frequency of measurement sittings within period p. The fourth strategy entails repeating period p later in a try-and-see trial.

As an illustrative example, the default level of precision for both systolic and diastolic blood pressure averages is a 95% credibility interval (a highest density interval) of 4 mm Hg. This credibility interval is intended to contain the most probable estimate of a patient-user's blood pressure (the mean, median, or mode of the posterior probability distribution, depending upon the preferences of the users), plus about 2 mm Hg above and below that estimate. This precision can be modified by either changing the desired credibility (for example, by reducing the credibility below 95%) or by narrowing or widening the range (for example, by widening the range to 6 mm Hg).

Figure 16:
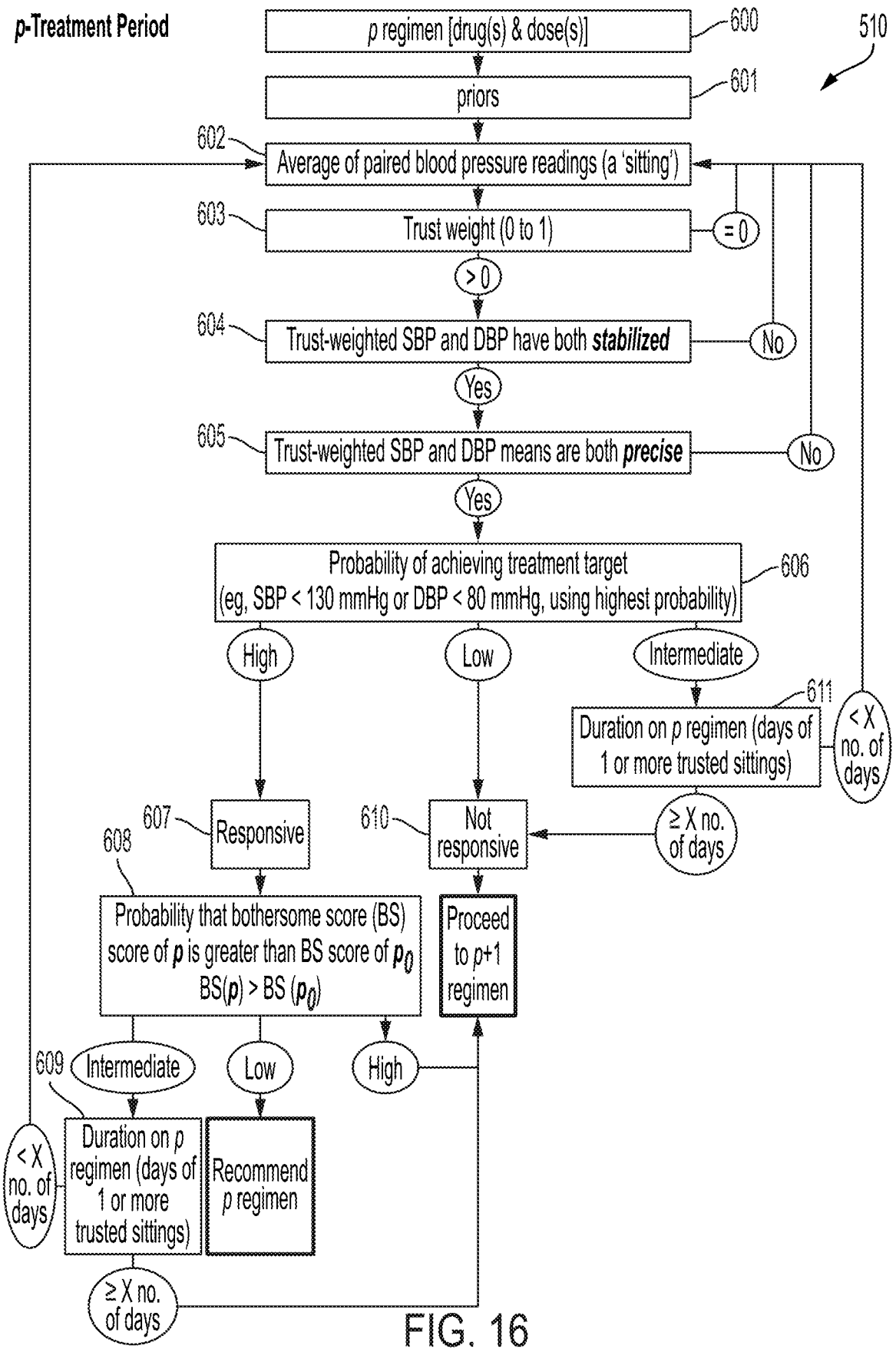
FIG. 16 is a flow diagram of the processing methods for an integrated drug selection system using the example of high blood pressure for the treatment of hypertension and other specific conditions and particularly, the step of evaluating the responsiveness of blood pressure to drugs in accordance with embodiments of the present invention.

Referring to FIG. 16, Bayesian methods continuously update multiple probabilities related to a patient-user's parameter estimates throughout period p at process 510. These include, given the measurement sittings obtained during period p, at step 600. First, priors are chosen at step 601 by the prescriber-user based on available data and current belief. At least one reservoir is pre-filled with period p drugs, at doses prescribed in the outpatient order set. As health condition measurement sittings are obtained, assigned trust weights at step 603, and (for sittings with trust weights greater than zero) combined with previous weighted sittings.

The stability of the estimates of the health condition parameter is assessed in step 604, with reference to FIG. 13. Assessments of drug regimens require sufficient time for the effect(s) of the drugs upon health condition parameters of interest to fully occur. In the initial stages of treatment, prescribers are often left wondering if a patient's response has leveled off so that the underlying true health condition parameters (in the case of high blood pressure, this would be the mean systolic blood pressure and mean diastolic blood pressure) are no longer increasing or decreasing by a magnitude that is clinically significant.

As described above, weights are used to de-emphasize measurement sittings from the initial days of a period p. Specifically, the two relevant component weights of the trust weight are WRAMP and WOVER. These weights reflect, respectively, population averages for the on-rate(s) of period p drug(s) and the off-rate(s) of p−1 drug(s). For example, to reflect the fact that roughly 50% of the reduction in blood pressure occurs within one week of the start of a blood pressure reducing drug and 80% occurs within two weeks, embodiments used to select the optimal high blood pressure treatment may set WRAMP to increase over the first weeks of period p so that measurements obtained on subsequent days in those first weeks contribute more to the posterior probability of the patient's systolic and diastolic blood pressure means.

While the response to drug regimens may be predictable on average, an individual patient-user's response can be very different from the population response. For example, some patient-users may not respond at all to a drug, regardless of how long it is given. Thus, the challenge for prescribers is determining, in real time, whether a given patient-user is responding and by how much. Therefore, the software and methods 200 of the present invention can include a second analysis to assess the probability in real-time that the effect(s) of period p drug(s) upon health condition parameters have stabilized for an individual, regardless of the population response. This analysis does not rely on population averages of on- and off-rates (WRAMP and WOVER, respectively); instead, it uses patient-user-specific information that has already been obtained earlier during a try-and-see trial.

This second analysis has two main components. The first component generates 'windows' of measurements (FIG. 14): sets of measurements for each period that comprise the baseline average at the start of the period ('baseline window'), the current average ('current window'), and the most recent average ('preceding window'). The second component then uses a Bayesian equivalence test (FIG. 13) to compare the current window to the preceding window, using prior information from the placebo period and the early phase of period p (the 'baseline window'). When the probability becomes high enough (ie, achieves a threshold established by the prescriber-user) that the difference between parameter estimates from the current and preceding windows is small, or narrow enough, to be clinically unimportant, the effect(s) of period p drug(s) on the health condition parameters has stabilized.

Figure 14:
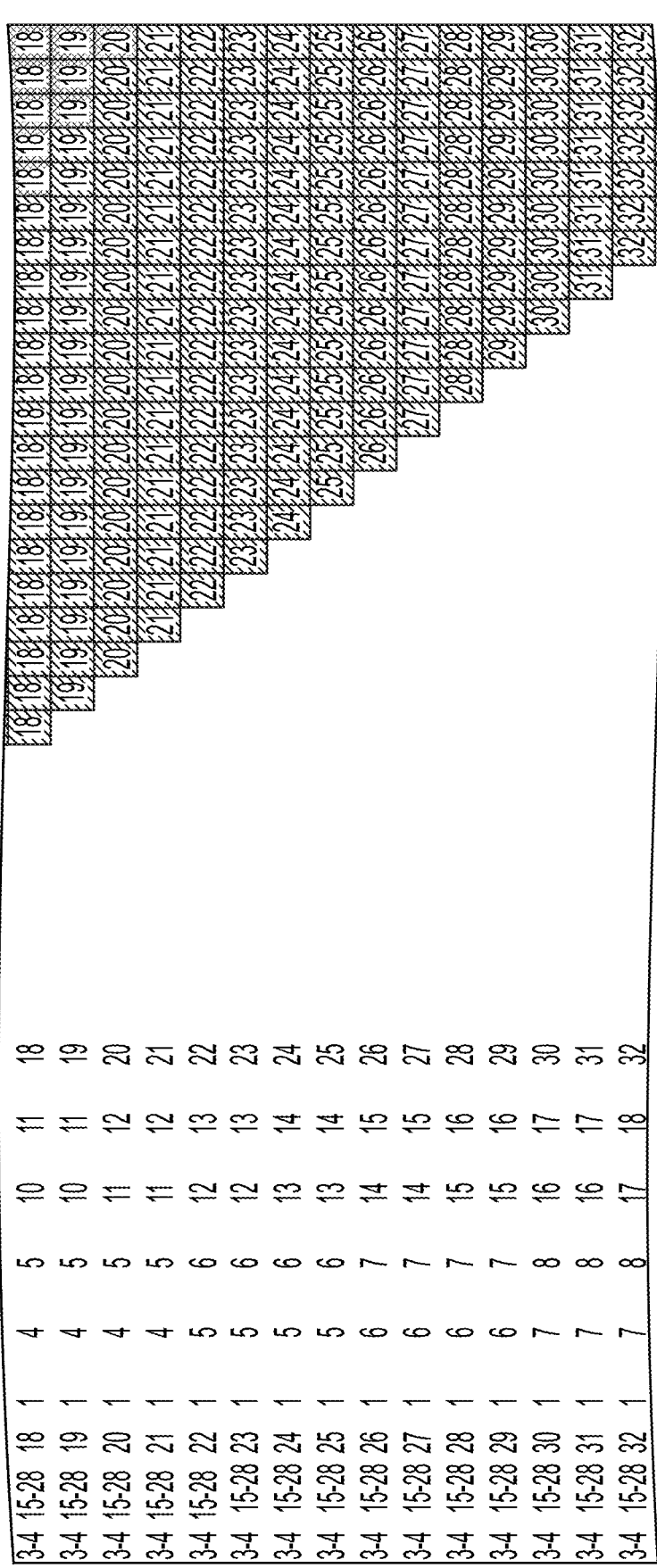
FIG. 14 is an exemplary embodiment of creating baseline, preceding, and current windows (or sets) of health condition measurements and continually adjusting those windows during a five-week period in accordance with embodiments of the present invention to conduct a Bayesian equivalence test.

Windows of Measurements As outlined in FIG. 13 and FIG. 14, the windows are continually adjusted according to a) the number of days in period p and b) the accumulation of 'window units' (WUs). Window units are comprised of small sets of measurement sittings for which the sum of corresponding window weights (cWWIN) equals 1 at step 651. The following formula from step 652 depicts the cumulative sum of window weights from sitting r+1 (where r is the last sitting of the previous window unit) to sitting i.

$$\text{Integer Floor}\left[\left(\sum_{k=r+1}^{i-1} \text{weight}_k\right)+\text{weight}_i\right] = \text{Integer Floor}\left[\sum_{k=r+1}^{i} \text{weight}_k\right]$$

As in step 653, if the integer floor of this sum is 1, then the corresponding set of measurement sittings comprise a window unit. Each WWIN is like a trust weight (WTRUST) except WWIN excludes the population averages that depict the on-rate(s) of period p drug(s) and the off-rate(s) of period p−1 drug(s) (WRAMP and WOVER, respectively). Only the sum of adherence and measurement weights (WAD+ WMEAS) are included in WWIN.

$$WWIN_{p,i,k} = \sum [WAD_{p,i,k} + WMEAS_{p,i,k}]$$

The total number of window units collected during the current period are evaluated at step 654, and if less than a threshold, it is determined that there are an insufficient number of window units to begin an evaluation at step 655, returning to acquire more data. If the number of window units are sufficient, processing continues. Steps 656, 657, and 658, as well as FIG. 14, depict an example of how baseline, preceding, and current windows could be defined and continually adjusted during a 5-week period when 50 WUs are accumulated. In FIG. 14, evaluations are discrete events when there is an assessment to determine whether a) the patient-user's health condition parameters of interest have stabilized in the current period p, b) the posterior probability distributions of the health condition parameters of interest have narrowed enough, and c) the posterior probabilities that the health condition parameters of interest will achieve target ranges with the least degree of adverse effects, relative to other treatments, are sufficient. FIG. 14 is an example demonstrating that the rate of accumulation of window units will (as depicted in FIG. 13) will depend upon rules determined by prescriber- and patient-user preferences, as well as the type of health condition parameter.

Test Equivalence Preceding and Current Windows A Bayesian comparison of means is used to compare measurement sittings from the preceding and current windows. Underlying assumptions about the specific parameterization of the sampling model and the prior distributions of the unknown parameters can be adjusted by the user. As is typically known in the art, other examples of various parameterizations and prior distributions can be used.

Shown here is a typical parameterization and sampling model. The 'true' underlying means for the preceding ($\theta_{preceding}$) and current windows ($\theta_{current}$) differ from an overall mean common to both windows ($\mu$) by a delta ($\delta$).

$$Y_{i,window} = \theta_{window} + \epsilon_{i,window} = \mu + \delta + \epsilon_{i,window}\{\epsilon_{i,window}\} \sim$$

$$i.i.d.\ t\big(loc = 0,\ \text{scale} = \sigma,\ dof = (WU_{preceding} + WU_{current})/2\big)$$

Where the subscript 'window' represents either the preceding or current window. A normal distribution for the sampling model could alternatively be used. A t-distribution, represented by location, scale, and degrees of freedom parameters, which may better accommodate extreme values is provided here. Potential priors that could be used include:

$$p(\theta_{preceding}, \theta_{current}, \sigma) = p(\theta_{preceding}) \times p(\theta_{current}) \times p(\sigma)$$

$$p(\theta_{window}) \sim t\left(\bar{x}_{(p-1)'},\ \frac{\bar{s}_{(p-1)'}}{WU_{(p-1)'}},\ WU_{(p-1)'}\right) \text{ if } WU_{baseline} < 5$$

$$p(\theta_{window}) \sim t\left(\bar{x}_{baseline},\ \frac{\bar{s}_{baseline}}{WU_{baseline}},\ WU_{baseline}\right) \text{ if } WU_{baseline} \geq 5$$

$$p(\sigma) \sim t(\bar{s}_0^2, 1, 1) = cauchy(\bar{s}_0^2, 1)$$

Where (p−1)' is the final current window of period p−1, and WU, $\bar{x}$, and $\bar{s}$ represent, respectively, the number of window units, the measurement mean of a window, and the measurement standard deviation of a window.

A sampling algorithm, such as Monte Carlo Markov Chain or Metropolis-Hastings, can then be used to generate a posterior probability distribution of $\delta$. Given that $\delta$ reflects the difference between each window and the overall mean $\mu$, which is midway between the population means of the preceding and current windows, the probability that $2 \times \delta$ is within a narrow equivalence margin (such as within ±2 mm Hg for blood pressure) can be estimated. If that probability is sufficient (a common sufficient probability could be ≥95%), then the means of the preceding and current windows are deemed equivalent (step 659 at FIG. 13), and the effect(s) of the drug regimen upon the health condition parameters has stabilized.

Referring back to FIG. 16, step 605 determines if the parameter estimates are precise enough. If both step 604 and step 605 are true, step 606 can proceed. Step 606 uses the leveled-off and precise parameter estimates (in this case the estimate of systolic and diastolic blood pressures while period p drugs are being administered) to classify health conditions.

In this illustrative embodiment, if the estimate of systolic blood pressure is less than 130 mmHg and diastolic blood pressure is less than 80 mmHg is determined to be low (such as, for example, 50% or less), the regimen at step 600 is determined to be not responsive 610 and the process returns to step 600 with the next p+1 regimen. If the probability is intermediate (such as, for example, greater than 50% but less than 95%), the duration of the p regimen is evaluated at step 611. If the duration is less than a predetermined number of days, for example, 30 days, the process returns to step 602 for an extended duration of the p regimen. If the duration is the predetermined number of days (in this example, 30) or more, the regimen at step 600 is determined to be not responsive 610 and the process returns to step 600 with the next p+1 regimen.

If at step 606 the probability that systolic blood pressure is less than 130 mmHg and diastolic blood pressure is less than 80 mmHg is determined to be high (such as, for example, greater than 95%) the regimen at step 600 is determined to be responsive 607 and at step 608 an assessment of side effects is performed. If the probability that the bothersome score during period p is greater than the bothersome score of $p_0$ is high (such as, for example, 95% or greater), then the process returns to step 600 with the next p+1 regimen. If the probability that the bothersome score during period p is greater than the bothersome score of $p_0$ is intermediate (such as, for example, greater than 50% but less than 95%), the duration of the p regimen is evaluated at step 609. If the duration is less than a predetermined number of days, for example, 30 days (or X no of days in FIG. 16), the process returns to step 602 for an extended duration of the p regimen. If the duration is equal to or more than the predetermined X number of days (in this example, 30), the process returns to step 600 with the next p+1 regimen. Finally, at step 608, if the posterior probability that the bothersome score during period p is greater than the bothersome score of $p_0$ is low (for example, 50% or less) the p regimen is selected as the best course of treatment.

Aspects of the software code of the invention, or code used with the invention, can take the form of a plugin or app, a web app, or a website interface, and can interface with various protocols or software using APIs or other means of interacting with computing software and systems.

Various computing devices 100, 103, 111, 160 described herein can be included and adapted to process and carry out the aspects, computations, and algorithmic processing of the integrated system 900 of the present invention. Computing systems and devices of the present invention may include a computing processor, which may include one or more microprocessors and/or one or more circuits, such as an application specific integrated circuit (ASIC), field-programmable gate arrays (FPGAs), etc. Further, the computing system and devices can include a network interface. The network interface is configured to enable communication with the network, other devices and systems, and servers, using a wired and/or wireless connection.

The devices or computing systems may include memory, such as non-transitive memory, which may include one or more non-volatile storage devices and/or one or more volatile storage devices (including, without limitation, random access memory (RAM)). In instances where the devices include a processor, computer readable program code may be stored in a computer readable medium or memory, such as, but not limited to storage media (including, without limitation, a hard disk or solid-state drive), optical media, memory devices (including, without limitation, random access memory, flash memory), etc. The computer program or software code can be stored on a tangible, or non-transitive, machine-readable medium or memory. In some embodiments, computer readable program code is configured such that when executed by a processor, the code causes the device to perform the steps described above and herein. In other embodiments, the device is configured to perform steps described herein without the need for code.

It will be recognized by one skilled in the art that these operations, algorithms, logic, method steps, routines, sub-routines, and modules may be implemented in software, in firmware, in special purpose digital logic, and any combination thereof without deviating from the spirit and scope of the present invention as recited within the claims attached hereto.

Server processing systems, such as those included with the cloud-based system 170, for use or connected with the dispensing assembly 100, devices, and components of the present invention, can include one or more processors, and/or one or more circuits, such as an application specific integrated circuit (ASIC), field-programmable gate arrays (FPGAs), etc. A network interface can be configured to enable communication with the network, using a wired and/or wireless connection, including communication with the devices or computing systems and devices 100, 103, 160 disclosed herein. Memory can include one or more non-volatile storage devices and/or one or more volatile storage devices (including, without limitation, random access memory (RAM)). In instances where the server system includes a processor, computer readable program code may be stored in a computer readable medium, such as, but not limited to storage media (including, without limitation, a hard disk or solid-state drive), optical media, memory devices, etc.

Aspects of the present invention can be embodied as software code residing on the patient-user's, the prescriber-user's, or the pharmacy-user's computing devices 103, 160, or 175 (including, without limitation, desktop, tablet, mobile, and the like) and/or on one or more server systems of the integrated drug selection system 170. The various received or processed data of the present invention can be included on and transferred to and from a storage area network (SAN), a data cloud, or any computing device for storing the file or files being uploaded, downloaded, or processed.

While the methods, steps, and processing described above and illustrated in the drawings are shown as a sequence of steps, this was done solely for the sake of illustration. Accordingly, it is contemplated that some steps may be added, some steps may be omitted, the order of steps may be re-arranged, and some steps may be performed in parallel.

For purposes of interpreting the claims for the present invention, it is expressly intended that the provisions of 35 U.S.C. § 112(f) are not to be invoked unless the specific terms "means for" or "step for" are recited in a claim.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

What is claimed is:

1. A drug dispensing and patient-response monitoring system comprising:

an outpatient order set comprising a protocol of a plurality of drug regimens proposed for the treatment of a patient-user, the outpatient order set adapted for using decisions based on Bayesian estimates of health condition parameters to implement the protocol of the plurality of drug regimens in the outpatient order sets without real-time prescriber-user approval to attain a treatment target;

a plurality of drug reservoirs, each of the drug reservoirs adapted to store a drug in individually dispensable form, each of the drug reservoirs corresponding to a drug regimen, and each of the drug reservoirs being concealed from the patient-user;

a central drive for dispensing any of the drugs of the drug regimens from its corresponding reservoir;

at least one input device adapted to collect a health condition measurement from the patient-user, the health condition measurement being one of a set of collected health condition measurements;

a controller in operative communication with the central drive and the at least one input device to dispense a drug corresponding to the drug regimen according to the outpatient order set, wherein the controller advances in the outpatient order set using:

a trust weight assigned to the collected health measurement;

an assessment of the stability and precision of health condition parameter estimates derived from the set of collected health condition measurements; and a probability that the treatment target is attained with each of the drug regimens dispensed.

2. The system according to claim 1 wherein the outpatient order set includes a placebo.

3. The system according to claim 2 wherein the placebo of the outpatient order set is an initial run-in treatment.

4. The system according to claim 1 wherein the central drive further comprises patient-user identification when dispensing any of the drugs of the outpatient order set.

5. The system according to claim 1 wherein the health condition measurements collected by the at least one input device include a time and date.

6. The system according to claim 1 wherein the trust weight is the sum of one or more of a carryover weight, a ramp up weight, an adherence weight and measurement weight.

7. The system according to claim 1 wherein the assessment of the stability of health condition parameter estimates includes a Bayesian analysis to determine if the posterior probability distribution of the difference between two sets of measurements, the two sets comprising windows of health condition measurements, meet a threshold of equivalence.

8. The system according to claim 1 wherein the assessment of the precision of health condition parameter estimates includes a Bayesian analysis to determine the width of the posterior probability distribution compared to a threshold level of precision.

9. The system according to claim 1 further comprising a security mechanism to provide blinding of the dispensing of drugs from the patient-user.

10. The system according to claim 9 wherein the security mechanism comprises a locked cover.

11. A method of operating a smart drug dispensing assembly to choose the optimal drug treatment for a health condition of a patient-user, the smart drug dispensing assembly having a plurality of drug reservoirs, at least one input device to collect health condition measurements, and a controller adapted to dispense any one or more of a drug treatment from its associated drug reservoir of the plurality of drug reservoirs, the method comprising;

providing an outpatient order set corresponding to a sequence of drug treatment regimens, measurement protocols, and prescriber-user notification safeguards;

dispensing a first drug corresponding to a first treatment regimen of the outpatient order set in a plurality of sittings and collecting the health condition measurements using the at least one input device at each of the plurality of sittings to provide a set of health condition measurements;

determining a trust weight of the set of health condition measurements;

once the trust weight for a set of health condition measurements exceeds a predetermined threshold and a computed stability and a computed precision of the set of health condition measurements exceeds a threshold, determine a probability that the treatment target has been attained with the first treatment regimen; and advancing to the next subsequent drug treatment in the sequence of drug treatment regimens of the outpatient order set if the probability that the treatment target has been attained is low or if the probability that the treatment target has been attained is high and a probability that a bothersome score of the set of health condition measurements is high.

12. The method according to claim 11 wherein a drug corresponding to a sequence of drug treatment regimens is a placebo.

13. The method according to claim 11 wherein the trust weight is the sum of one or more of a carryover weight, a ramp up weight an adherence weight, and a measurement weight.

14. The method according to claim 11 wherein the health condition of the patient-user includes at least one of hypertension, depression, pain management, acne, addiction, attention deficit hyperactivity disorder, AIDS/HIV, allergies, angina, anxiety, arthritis, asthma, bipolar disorder, bronchitis, cancer, cholesterol, chronic kidney disease, constipation, chronic obstructive pulmonary disease, dementia, diabetes, diarrhea, dizziness, dysuria, eczema, erectile disfunction, fatigue, fibromyalgia, gastroesophageal reflux, heartburn, gout, hair loss, hay fever, headaches, heart disease, heart failure, herpes, hypothyroidism, inflammatory bowel disease, incontinence, insomnia, loss of libido, menopause, mental health, migraines, muscle aches, nausea, neuropathy, obesity, osteoarthritis, osteoporosis, pain, pneumonia, prostate disease, psoriasis, rheumatoid arthritis, schizophrenia, seizures, sexual disfunction, tinnitus, and body weight gain/ loss.

15. The method according to claim 11 wherein the step of advancing to the next subsequent drug treatment includes returning to drug treatment regimen having an earlier-established probability of treatment success.

16. The method according to claim 12 wherein the step of advancing to the next subsequent drug treatment includes returning to the first drug treatment regimen.

17. The method according to claim 11 wherein the step of advancing to the next subsequent drug treatment in the sequence of drug treatment regimens of the outpatient order set further comprises if the probability that the treatment target has been attained is neither high or low, and a predetermined time period has elapsed.

18. An integrated drug selection system for a prescriber-user, a patient-user, and a pharmacist-user, having a treatment target, comprised of:

an outpatient order set corresponding to a sequence of drug treatment regimens, measurement protocols, and prescriber-user notification safeguards;

a plurality of drug reservoirs, each of the drug reservoirs adapted to store a drug in individually dispensable form, each of the drug reservoirs corresponding to a drug regimen, and each of the drug reservoirs being concealed from the patient-user;

at least one input device adapted to collect at least one health condition measurement from the patient-user;

a controller in operative communication with the at least one input device comprising a memory to store the at least one health condition measurement in a list of measurements associated with the patient-user, the controller to select one of the plurality of drug reservoirs corresponding to the drug regimen according to the outpatient order set using:

a trust weight assigned to the at least one health measurement;

an assessment of the stability and precision of health condition parameter estimates, derived from the list of measurements; and a probability that the treatment target is attained with each of the drug regimens dispensed.

19. The system according to claim 18 wherein the outpatient order set includes a placebo.

20. The system according to claim 18 wherein the trust weight assigned to the at least one health measurement is the sum of a carryover weight, a ramp up weight, an adherence weight and measurement weight.

\* \* \* \* \*